(12) United States Patent
Bantick et al.

(10) Patent No.: US 6,300,334 B1
(45) Date of Patent: Oct. 9, 2001

(54) THIENO[2,3-D]PYRIMIDINE-2,4-DIONES

(75) Inventors: John Bantick, Burton-on-the-Wolds; Martin Cooper, Loughborough; Matthew Perry, Loughborough; Philip Thorne, Loughborough, all of (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/402,837

(22) PCT Filed: Aug. 18, 1999

(86) PCT No.: PCT/SE99/01400

§ 371 Date: Oct. 13, 1999

§ 102(e) Date: Oct. 13, 1999

(87) PCT Pub. No.: WO00/12514

PCT Pub. Date: Mar. 9, 2000

(30) Foreign Application Priority Data

Aug. 28, 1998 (SE) ................................................ 9802895

(51) Int. Cl.$^7$ ..................... C07D 495/04; A61K 31/519; A61P 37/06
(52) U.S. Cl. ............................. 514/258; 544/278
(58) Field of Search ...................... 514/258, 278

(56) References Cited

FOREIGN PATENT DOCUMENTS 293 824 A5    9/1991  (DE) .
0 640 606 A1  3/1995  (EP) .

OTHER PUBLICATIONS

Fukumi et al, Chemical Abstracts, vol. 112, No. 139045t, pp. 722–723 (1990).

Gutschowe et al, "3–Mercaptoalkylthieno[2,3–d]pyrimidin–2,4(1H,3H)–dione: Synthese . . . ," Arch. Pharm. (Weinheim), vol. 328, pp. 231–234 (1995).

*Primary Examiner*—Mukund J. Shah
*Assistant Examiner*—Thoams C. McKenzie
(74) *Attorney, Agent, or Firm*—Nixon & Vanderhye

(57) ABSTRACT

Compounds of formula (I):

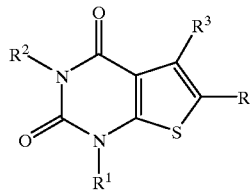

(I)

wherein $R^1$, $R^2$, and $R^3$ are defined in the specification. The compounds are useful for treating or reducing the risk of reversible obstructive airways disease.

12 Claims, No Drawings

THIENO[2,3-D]PYRIMIDINE-2,4-DIONES

This invention relates to pharmaceutically useful compounds, processes for their production, pharmaceutical compositions containing them and methods of treatment involving their use.

T-cells play an important role in the immune response, however in autoimmune disease T-cells are activated against particular tissues, e.g. causing the inflammation associated with rheumatoid arthritis. Interleukin-2 (IL-2) is an essential autocrine growth factor for T-cells and hence inhibition of IL-2 transcription is beneficial in the modulation of autoimmune disease. Formation of a transcriptional complex of the protein nuclear factor of activated T-cells-1 (NFAT-1) on the EL-2 promoter is essential for IL-2 transcription. NFAT-1 mediated transcription has therefore been proposed as appropriate molecular target for immunomodulation, Y. Baine et al., *J. Immunol*, 1995, 154, 3667–3677.

W. F. Michne et al, in *J. Med. Chem.* (1995) 38, 2557–2569 disclose a number of quinazoline-2,4-diones and pyrrolo[3,4-d]pyrimidine-2,4-diones which inhibit transcription regulated by the DNA region bound by the NFAT-1 protein.

We have now found novel thieno[2,3-d] pyrimidinediones which exhibit pharmacological activity, in particular immunosuppressive activity.

In a first aspect the invention therefore provides a compound of formula (I):

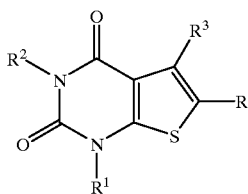

(I)

wherein:

R represents a group —C(O)Ar$^1$ or —C(R$^4$)(R$^5$)Ar$^1$;

Ar$^1$ represents a heterocyclic group comprising a total of from 5 to 10 atoms which include from 1 to 3 heteroatoms independently selected from nitrogen, oxygen and sulfur, which group Ar$^1$ may be optionally substituted by one or more substituents independently selected from oxo, hydroxyl, $C_{1-4}$ alkyl, $C_{1-4}$ alkoxy, halogen, trifluoromethyl, amino, nitro, cyano, trifluoromethoxy, phenoxy, —CH$_2$N(R$^6$)$_2$, —NHSO$_2$CF$_3$, $C_{1-4}$alkylsulfonylamino, —NHC(O)R$^{6a}$, CO$_2$R$^7$ or —C(O)NR$^8$R$^{8a}$, with the proviso that Ar$^1$ does not represent an optionally substituted benzofuranyl, benzothienyl, indolyl, quinolyl or isoquinolyl group;

R$^4$ represents a hydrogen atom or a $C_{1-4}$ alkyl group;

R$^5$ represents a hydrogen atom or a hydroxyl group;

each R$^6$ independently represents a hydrogen atom or a $C_{1-4}$ alkyl (e.g. methyl, ethyl, propyl or butyl) group, preferably a methyl or ethyl group;

R$^{6a}$ represents a hydrogen atom or a $C_{1-6}$ alkyl, aryl or ar$C_{1-4}$alkyl group, wherein the aryl group or aryl moiety in the aralkyl group is phenyl or pyridinyl, each of which may be optionally substituted by one or more substituents independently selected from $C_{1-4}$ alkyl, $C_{1-4}$ alkoxy, $C_{1-4}$ alkylcarbonylamino, halogen or trifluoromethyl;

R$^7$ represents a hydrogen atom or a $C_{1-4}$ alkyl (e.g. methyl, ethyl, propyl or butyl) group, preferably a methyl or ethyl group;

R$^8$ and R$^{8a}$ each independently represent a hydrogen atom or a $C_{1-4}$ alkyl (e.g. methyl, ethyl, propyl or butyl, preferably methyl or ethyl), phenyl or pyridinyl group;

R$^1$ and R$^2$ each independently represent a hydrogen atom or a $C_{1-6}$ alkyl, $C_{3-6}$ alkenyl, CH$_2$C$_{3-5}$ cycloalkyl or $C_{3-6}$ cycloalkyl group;

R$^3$ represents a hydrogen atom or a group X—R$^9$ or X—Ar$^2$;

X represents an oxygen atom, S(O)$_n$, C(O)NR$^{10}$, C(O)O, NH(CO)NR$^{10}$, NH(CO)O or SO$_2$NR$^{10}$, with the proviso that when X represents an oxygen atom and R represents a group —C(R$^4$)(R$^5$)Ar$^1$, then R$^4$ and R$^5$ both represent a hydrogen atom; n is 0, 1 or 2;

R$^9$ represents a methyl group optionally substituted by one or more substituents independently selected from cyano, carboxyl, $C_{1-5}$ alkoxycarbonyl, 5-tetrazolyl or C(O)NR$^{11}$R$^{12}$, or R$^9$ represents a $C_{2-6}$ alkyl or $C_{3-6}$ alkenyl group, each of which may be optionally substituted by one or more substituents independently selected from hydroxyl, cyano, carboxyl, $C_{1-5}$ alkoxy, $C_{1-5}$ alkoxycarbonyl, 5-tetrazolyl, azido, phthalimido, SO$_2$NH$_2$, C(O)NR$^{11}$R$^{12}$, NR$^{13}$R$^{14}$, NHC(O)R$^{15}$ or NHSO$_2$R$^{16}$ where R$^{11}$, R$^{12}$, R$^{13}$ and R$^{14}$ each independently represent a hydrogen atom or a $C_{1-4}$ alkyl group, R$^{15}$ represents a $C_{1-4}$ alkyl, $C_{1-4}$ alkoxy, amino or (di)$C_{1-4}$alkylamino group or an alkoxyalkylene group containing up to 6 carbon atoms, and R$^{16}$ represents a $C_{1-4}$ alkyl or trifluoromethyl group; or, additionally, in the case where X represents C(O)NR$^{10}$, NH(CO)NR$^{10}$ or SO$_2$NR$^{10}$, R$^9$ and R$^{10}$ together with the nitrogen atom to which they are attached may form a 4- to 7-membered saturated heterocyclic ring which may be optionally substituted by one or more hydroxyl groups;

R$^{10}$ represents a hydrogen atom or a $C_{1-6}$ alkyl group or is linked to R$^9$ as defined above; and Ar$^2$ is phenyl, pyridinyl, thienyl, pyridone or pyridine N-oxide, each of which may be optionally substituted by one or more substituents independently selected from halogen, hydroxyl, nitro, amino, NHSO$_2$CF$_3$, $C_{1-4}$ alkyl, $C_{1-4}$ alkoxy, bis-$C_{1-4}$alkanesulfonylamino, $C_{1-4}$alkylcarbonylamino or $C_{1-4}$alkoxycarbonylamino;

or a pharmaceutically-acceptable salt or solvate thereof.

In the present specification, unless otherwise indicated, an alkyl or alkenyl group or an alkyl or alkenyl moiety in a substituent group may be linear or branched. When R$^9$ represents an optionally substituted $C_{2-4}$ alkyl or $C_{3-6}$ alkenyl group, it should be understood that certain optional substituents (e.g. hydroxyl, $C_{1-5}$ alkoxy, azido, phthalimido, SO$_2$NH$_2$, NR$^{13}$R$^{14}$, NHC(O)R$^{15}$ or NHSO$_2$R$^{16}$) may not be attached to the carbon atom of the alkyl or alkenyl group which is directly bonded to X. Furthermore, where the substituent in the alkenyl group is hydroxyl, phthalimido, NR$^{13}$R$^{14}$ or NHC(O)R$^{15}$, the substituent will not be attached to an unsaturated carbon atom. When R$^9$ and R$^{10}$ form a 4- to 7-membered heterocyclic ring optionally substituted by hydroxyl, the hydroxyl group(s) will not be attached to the carbon atoms directly bonded to the nitrogen atom.

The alkyl moieties in a di-$C_{1-4}$ alkylamino group may be the same or different.

The group R represents —C(O)Ar$^1$ or —C(R$^4$)(R$^5$)Ar$^1$. It should be understood that when R represents —C(O)Ar$^1$ the group Ar$^1$ is bonded through a carbon atom and not a heteroatom to the moiety —C(O). Also, in the case when X represents an oxygen atom and R represents —C(R$^4$)(R$^5$) Ar$^1$, the group Ar$^1$ is bonded through a carbon atom and not a heteroatom to the C(R$^4$)(R$^5$) moiety of the group R.

The group R⁴ represents a hydrogen atom or a $C_{1-4}$ alkyl, preferably methyl or ethyl, group and the group R⁵ represents a hydrogen atom, or a hydroxyl group (in the case where Ar¹ is attached through a carbon atom to the moiety —C(R⁴)(R⁵)).

Preferably Ar¹ represents a heterocyclic group comprising a total of from 5 to 10 atoms which include from 1 to 3 heteroatoms independently selected from nitrogen, oxygen and sulfur, which may be optionally substituted by one, two, three or four substituents independently selected from oxo, hydroxyl, $C_{1-4}$ alkyl (e.g. methyl, ethyl, propyl or butyl), $C_{1-4}$ alkoxy (e.g. methoxy, ethoxy, propoxy or butoxy), halogen (e.g. fluorine, chlorine, bromine or iodine), trifluoromethyl, amino, nitro, cyano, trifluoromethoxy, phenoxy, —CH₂N(R⁶)₂, —NHSO₂CF₃, $C_{1-4}$alkylsulfonylamino, —NHC(O)R⁶ᵃ, CO₂R⁷ or —C(O)NR⁸R⁸ᵃ, with the proviso that Ar¹ does not represent an optionally substituted benzofuranyl, benzothienyl, indolyl, quinolyl or isoquinolyl group. Preferred substituents to use are halogen atoms and $C_{1-4}$ alkyl groups.

The group Ar¹ may represent an optionally substituted saturated heterocyclic group but is preferably an optionally substituted unsaturated heterocyclic group, examples of which include pyrazolyl, thienyl, oxazolyl, imidazolyl, pyridinyl, pyridopyrrolyl, benzimidazolyl, indazolyl, benzothiazolyl, benzoxazolyl, thiazolyl, benzotriazolyl,

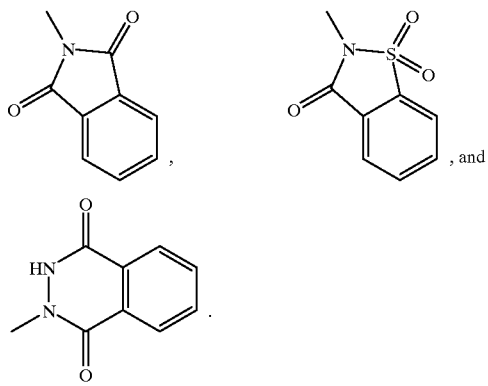
, and

R⁶ᵃ is preferably a hydrogen atom or a $C_{1-6}$, particularly $C_{1-4}$, alkyl (e.g. methyl, ethyl, propyl, butyl, pentyl or hexyl), aryl or ar$C_{1-4}$alkyl group, wherein the aryl group or aryl moiety in the aralkyl group is phenyl or pyridinyl, each of which may be optionally substituted by one, two, three or four, especially one or two, substituents independently selected from $C_{1-4}$ alkyl (e.g. methyl, ethyl, propyl or butyl), $C_{1-4}$ alkoxy (e.g. methoxy, ethoxy, propoxy or butoxy), $C_{1-4}$ alkylcarbonylamino (e.g. methyl- or ethylcarbonylamino), halogen (e.g. fluorine, chlorine, bromine or iodine) or trifluoromethyl.

Preferably R¹ and R² each independently represent a hydrogen atom or a $C_{1-4}$ alkyl (e.g. methyl, ethyl, propyl or butyl), $C_{3-4}$ alkenyl, CH₂$C_{3-5}$ cycloalkyl or $C_{5-6}$ cycloalkyl group.

It is preferred that R¹ is a $C_{3-4}$ alkyl group or CH₂$C_{3-5}$ cycloalkyl group, in particular 1-methylethyl, 2-methylpropyl or cyclopropylmethyl.

It is preferred that R² is a methyl group.

R³ represents a hydrogen atom or a group X—R⁹ or X—Ar². X represents most preferably an oxygen or sulphur atom or a group SO₂, C(O)NR¹⁰ or SO₂NR¹⁰.

Preferably, R⁹ represents a methyl group optionally substituted by one or two substituents independently selected from cyano, carboxyl, $C_{1-5}$ alkoxycarbonyl, 5-tetrazolyl or C(O)NR¹¹R¹², or R⁹ represents a $C_{2-6}$ alkyl or $C_{3-6}$ alkenyl group, each of which may be optionally substituted by one, two, three or four, particularly one or two, substituents independently selected from hydroxyl, cyano, carboxyl, $C_{1-5}$ alkoxy, $C_{1-5}$ alkoxycarbonyl, 5-tetrazolyl, azido, phthalimido, SO₂NH₂, C(O)NR¹¹R¹², NR¹³R¹⁴, NHC(O) R¹⁵ or NHSO₂R¹⁶ where R¹¹, R¹², R¹³ and R¹⁴ each independently represent a hydrogen atom or a $C_{1-4}$ alkyl (e.g. methyl, ethyl, propyl or butyl, particularly methyl or ethyl) group, R¹⁵ represents a $C_{1-4}$ alkyl (e.g. methyl, ethyl, propyl or butyl, particularly methyl or ethyl), $C_{1-4}$ alkoxy (e.g. methoxy, ethoxy, propoxy or butoxy, particularly methoxy or ethoxy), amino or (di)$C_{1-4}$alkylamino, particularly (di)methylamino or (di)ethylamino, group or an alkoxyalkylene group containing from 2 to 4 carbon atoms, and R¹⁶ represents a $C_{1-4}$ alkyl (e.g. methyl, ethyl, propyl or butyl, particularly methyl or ethyl), or trifluoromethyl group; or, additionally, in the case where X represents C(O)NR¹⁰, NH(CO)NR¹⁰ or SO₂NR¹⁰, R⁹ and R¹⁰ together with the nitrogen atom to which they are attached may form a 5- or 6-membered saturated heterocyclic ring which may be optionally substituted by one or two hydroxyl groups.

Preferably, R¹⁰ represents a hydrogen atom or a $C_{1-4}$ alkyl (e.g. methyl, ethyl, propyl or butyl, particularly methyl or ethyl) group or is linked to R⁹ as defined above.

Preferably, Ar² is phenyl, pyridinyl, thienyl, pyridone or pyridine N-oxide, each of which may be optionally substituted by one, two, three or four, particularly one or two, substituents independently selected from halogen (e.g. fluorine, chlorine, bromine or iodine), hydroxyl, nitro, amino, NHSO₂CF₃, $C_{1-4}$ alkyl (e.g. methyl, ethyl, propyl or butyl, particularly methyl or ethyl), $C_{1-4}$ alkoxy (e.g. methoxy, ethoxy, propoxy or butoxy, particularly methoxy or ethoxy), bis-$C_{1-4}$alkanesulfonylamino (particularly bis-$C_{1-2}$alkanesulfonylamino), $C_{1-4}$alkylcarbonylamino (particularly $C_{1-2}$alkylcarbonylamino) or $C_{1-4}$alkoxycarbonylamino (particularly $C_{1-2}$alkoxycarbonylamino). Ar² is especially a thienyl group.

Particularly preferred compounds of the invention include:

(±)-6-[1-Hydroxy-1-(1-methyl-1H-benzimidazol-2-yl) methyl]-3-methyl-1-(2-methylpropyl)thieno[2,3-d] pyrimidine-2,4(1H,3H)-dione, 3-Methyl-6-[(1-methyl-1H-benzimidazol-2-yl)methyl]-1-(2-methylpropyl)thieno[2,3-d]pyrimidine-2,4(1H,3H)-dione, (±)-6-[1-Hydroxy-1-(2-pyridinyl)methyl]-3-methyl-1-(2-methylpropyl)thieno[2,3-d]-pyrimidine-2,4(1H,3H)-dione, (±)-6-[1-Hydroxy-1-(3-pyridinyl)methyl]-3-methyl-1-(2-methylpropyl)thieno[2,3-d]-pyrimidine-2,4(1H,3H)-dione, (±)-6-[1-Hydroxy-1-(4-pyridinyl)methyl]-3-methyl-1-(2-methylpropyl)thieno[2,3-d]-pyrimidine-2,4(1H,3H)-dione, (±)-6-[1-Hydroxy-1-(2-thienyl)methyl]-3-methyl-1-(2-methylpropyl)thieno[2,3-d]-pyrimidine-2,4(1H,3H)-dione, (±)-6-[1-(5-Chloro-2-thienyl)-1-hydroxymethyl]-3-methyl-1-(2-methylpropyl)thieno[2,3-d]pyrimidine-2,4(1H,3H)-dione, (±)-6-[1-Hydroxy-1-(3-thienyl)methyl]-3-methyl-1-(2-methylpropyl)thieno[2,3-d]-pyrimidine-2,4(1H,3H)-dione, (±)-6-[1-Hydroxy-1-(2-thiazolyl)methyl]-3-methyl-1-(2-methylpropyl)thieno[2,3-d]pyrimidine-2,4(1H,3H)-dione, (±)-6-[1-(4-Chloro-1-methyl-1H-pyrazol-3-yl)-1-hydroxymethyl]-3-methyl-1-(2-methylpropyl)thieno[2,3-d]pyrimidine-2,4(1H,3H)-dione, 3-Methyl-1-(2-methylpropyl)-6-(2-pyridinylmethyl)thieno[2,3-d]pyrimidine-2,4(1H,3H)-dione, 3-Methyl-1-(2-methylpropyl)-6-(3-pyridinylmethyl)thieno[2,3-d]pyrimidine-2,4(1H,3H)-dione, 3-Methyl-1-(2-methylpropyl)-6-(4-pyridinylmethyl)thieno[2,3-d]pyrimidine-2,4(1H,3H)-dione, 3-Methyl-1-(2-methylpropyl)-6-(2-thienylmethyl)thieno[2,3-d]pyrimidine-2,4(1H,3H)-dione, 6-(5-Chloro-2-thienylmethyl)-3-methyl-1-(2-methylpropyl)thieno[2,3-d]pyrimidine-2,4(1H,3H)-dione, 3-Methyl-1-(2-methylpropyl)-6-(2-thiazolylmethyl)thieno[2,3-d]pyrimidine-2,4(1H,3H)-dione, 6-[(4-Chloro-1-methyl-1H-pyrazol-3-yl)methyl]-3-methyl-1-(2-methylpropyl)thieno[2,3-d]pyrimidine-2,4(1H,3H)-dione, 6-[(1H-Benzimidazol-1-yl)methyl]-3-methyl-1-(2-methylpropyl)thieno[2,3-d]pyrimidine-2,4(1H,3H)-dione, 6-(2H-Benzotriazol-2-ylmethyl)-3-methyl-1-(2-methylpropyl)thieno[2,3-d]pyrimidine-2,4(1H,3H)-dione, 6-(1H-Benzotriazol-1-ylmethyl)-3-methyl-1-(2-methylpropyl) thieno[2,3-d]-pyrimidine-2,4(1H,3H)-dione, 6-(2H-Indazol-2-ylmethyl)-3-methyl-1-(2-methylpropyl)thieno[2,3-d]pyrimidine-2,4(1H,3H)-dione, 6-(1H-Indazol-1-ylmethyl)-3-methyl-1-(2-methylpropyl)thieno[2,3-d]pyrimidine-2,4(1H,3H)-dione, 3-Methyl-1-(2-methylpropyl)-6-[(1H-pyrrolo[2,3-b]pyridin-3-yl)methyl]thieno[2,3-d]pyrimidine-2,4-1H,3H)-dione, (±)-6-[1-Hydroxy-1-(benzothiazol-2-yl)methyl]-3-methyl-1-(2-methylpropyl)thieno[2,3-d]pyrimidine-2,4(1H,3H)-dione, 6-(Benzothiazol-2-yl)methyl-3-methyl-1-(2-methylpropyl)thieno[2,3-d]pyrimidine-2,4(1H,3H)-dione, 6-[1-Hydroxy-1-(1-methyl-1H-benzimidazol-2-yl)methyl]-3-methyl-1-(1-methylethyl)thieno[2,3-d]pyrimidine-2,4(1H, 3H)-dione, 3-Methyl-6-[(1-methyl-1H-benzimidazol-2-yl)methyl]-1-(1-methylethyl)thieno[2,3-d]pyrimidine-2,4(1H, 3H)-dione, (3R)-1-{[1,2,3,4-Tetrahydro-3-methyl-1-(2-methylpropyl)-6-(3-pyridinyl)methyl-2,4-dioxothieno[2,3-d]pyrimidin-5-yl]sulfonyl}pyrrolidin-3-ol, 1-{[1,2,3,4-Tetrahydro-3-methyl-1-(2-methylpropyl)-6-(3-pyridinyl)methyl-2,4-dioxothieno[2,3-d]pyrimidin-5-yl]sulfonyl}pyrrolidine, ±-6-[(1H-Benzimidazol-2-yl)-1-hydroxymethyl]-3-methyl-1-(2-methylpropyl)thieno[2,3-d]pyrimidine-2,4(1H,3H)-dione, 6-[(1H-Benzimidazol-2-yl)methyl]-3-methyl-1-(1-methylethyl)thieno[2,3-d]pyrimidine-2,4(1H,3H)-dione, 6-([1H-Benzimidazol-1-yl]methyl)-1-(cyclopropylmethyl)-3-methyl-thieno[2,3-9]pyrimidine-2,4(1H, 3H)-dione, 1-(Cyclopropylmethyl)-6-[1-hydroxy-1-(1-methyl-1H-benzimidazol-2-yl)methyl]-3-methylthieno[2,3-d]pyrimidin-2,4(1H,3H)-dione, 1-(Cyclopropylmethyl)-6-[(1-methyl-1H-benzimidazol-2-yl)methyl]-3-methylthieno [2,3-d]pyrimidin-2,4(1H, 3H)-dione, 1-({6-[(1H-Benzimidazol-1-yl)methyl]-1,2,3,4-tetrahydro-3-methyl-1-(2-methylpropyl)-2,4-dioxothieno[2,3-d]pyrimidin-5-yl}carbonyl)pyrrolidine, 1-({1,2,3,4-Tetrahydro-6-[(1-methyl-1H-benzimidazol-2-yl)methyl]-1-(cyclopropylmethyl)-3-methyl-2,4-dioxothieno[2,3-d]pyrimidin-5-yl}carbonyl)azetidine, 5-[(3-Hydroxypropyl)thio]-3-methyl-1-(2-methylpropyl)-6-[(pyridin-3-yl)carbonyl]thieno[2,3-d]pyrimidine-2,4(1H,3H)-dione, 5-[(3-Hydroxypropyl)thio]-3-methyl-1-(2-methylpropyl)-6-[1-hydroxy-1-(pyridin-3-yl)methyl]thieno[2,3-d]pyrimidine-2,4(1H,3H)-dione, 5-[(3-Hydroxypropyl)thio]-3-methyl-1-(2-methylpropyl)-6-[1-(pyridin-3-yl)methyl]thieno[2,3-d]pyrimidine-2,4(1H,3H)-dione, 3-Methyl-1-(2-methylpropyl)-6-[(pyridin-3-yl)carbonyl]-5-[(2-thienyl)thio]thieno[2,3-d]pyrimidine-2,4(1H, 3H)-dione, 3-Methyl-1-(2-methylpropyl)-6-[1-(pyridin-3-yl)methyl]-5-[(2-thienyl)thio]thieno[2,3-d]pyrimidine-2,4(1H,3H)-dione, 5-(3-Hydroxypropoxy)-3-methyl-1-(2-methylpropyl)-6-[1-(pyridin-3-yl)methyl]thieno[2,3-d]pyrimidine-2,4(1H,3H)-dione, 3-Methyl-6-[(1-methyl-1H-benzimnidazol-2-yl)carbonyl]-5-[(1-methylethyl)thio]-1-(2-methylpropyl)-thieno[2,3-d]pyrimidine-2,4(1H,3H)-dione, 6-[Hydroxy(1-methyl-1H-benzimidazol-2-yl)methyl]-3-methyl-5-[(1-methylethyl)thio]-1-(2-methylpropyl)-thieno[2,3-d]pyrimidine-2,4(1H,3H)-dione, 3-Methyl-6-[(1-methyl-1H-benzimidazol-2-yl)methyl]-5-[(1-methylethyl)thio]-1-(2-methylpropyl)-thieno[2,3-d]pyrimidine-2,4(1H,3H)-dione, 3-Methyl-6-[(1-methyl-1H-benzimidazol-2-yl)methyl]-5-[(1-methylethyl)sulfonyl]-1-(2-methylpropyl)-thieno[2,3-d]pyrimidine-2,4(1H,3H)-dione, 3-Methyl-5-[(1-methylethyl)thio]-1-(2-methylpropyl-6-(3-pyridinylcarbonyl)-thieno[2,3-d]pyrimidine 2,4(1H, 3H)-dione, 6-(Hydroxy-3-pyridinylmethyl)-3-methyl-5-[(1-methylethyl)thio]-1-(2-methylpropyl)-thieno[2,3-d]pyrimidine-2,4(1H,3H)-dione, 3-Methyl-5-[(1-methylethyl)thio]-1-(2-methylpropyl)-6-(3-pyridinylmethyl)-thieno[2,3-d]pyrimidine-2,4(1H, 3H)-dione, 6-(1H-Benzimidazol-1-ylmethyl)-3-methyl-1-(2-methylpropyl)-5-(2-thienylthio)-thieno[2,3-d]pyrimidine-2,4(1H,3H)-dione, 6-[(2-Chloro-1H-benzimidazol-1-yl)methyl-3-methyl-1-(2-methylpropyl)-5-(2-thienylthio)-thieno[2,3-d]pyrimidine-2,4(1H,3H)-dione, 6-[(1,3-Dihydro-1,3-dioxo-2H-isoindol-2-yl)methyl]-3-methyl-1-(2-methylpropyl)-5-(2-thienylthio)-thieno[2,3-d]pyrimidine-2,4(1H,3H)-dione, 6-[Hydroxy[6-(trifluoromethyl)-2-pyridinyl]methyl]-3-methyl-1-(2-methylpropyl)-5-(2-thienylthio)-thieno[2,3-d]pyrimidine-2,4(1H,3H)-dione, 6-(1H-Benzimidazol-1-ylmethyl)-3-methyl-5-[(1-methylethyl)thio]-1-(2-methylpropyl)-thieno[2,3-d]pyrimidine-2,4(1H,3H)-dione, 3-Methyl-5-[(1-methylethyl)thio]-1-(2-methylpropyl)-6-[[3-oxo-1,2-benzisothiazol-2(3H)-yl]methyl]-thieno[2,3-d]pyrimidine-2,4(1H,3H)-dione, S,S-dioxide, 2,3-Dihydro-2-[[1,2,3,4-tetrahydro-3-methyl-5-[(1-methylethyl)thio]-1-(2-methylpropyl)-2,4-dioxothieno[2,3-d]pyrimidin-6-yl]methyl]-1,4-phthalazinedione and their pharmaceutically acceptable salts and solvates.

According to the invention there is also provided a process for the preparation of a compound of formula (1) which comprises:

(a) when R represents a hydrogen atom or a group X—$R^9$ or X—$Ar^2$ where X represents $C(O)NR^{10}$, $C(O)O$, $NH(CO)NR^{10}$ or $NH(CO)O$ and R represents —$C(R^4)(R^5)Ar^1$ where $R^4$ is a hydrogen atom or a $C_{1-4}$ alkyl group, $R^5$ is a hydroxyl group and $Ar^1$ is attached through a carbon atom to —$C(R^4)(R^5)$, reacting a compound of general formula

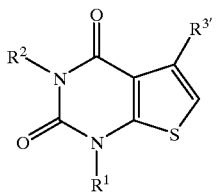

(II)

wherein $R^{3'}$ represents a hydrogen atom or a group X—$R^9$ or X—$Ar^2$ in which X represents $C(O)NR^{10}$, $C(O)O$, $NH(CO)NR^{10}$ or $NH(CO)O$, and $R^1$, $R^2$, $R^9$, $R^{10}$ and $Ar^2$ are as hereinbefore defined, with a compound of general formula (III), $Ar^1$—$C(O)R^4$, wherein $R^4$ and $Ar^1$ are as defined above and $Ar^1$ is attached through a carbon atom to —$C(O)R^4$; or (b) when R represents —$C(R^4)(R^5)Ar^1$ where $R^4$ is a hydrogen atom, $R^5$ is a hydroxyl group and $Ar^1$ is attached through a carbon atom to —$C(R^4)(R^5)$, reacting a compound of general formula

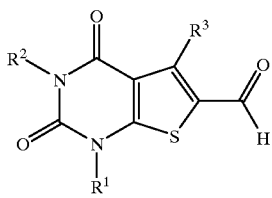

(IV)

wherein $R^1$, $R^2$ and $R^3$ are as hereinbefore defined, with a compound of general formula (V), $Ar^1$—M, wherein M represents a metal ion (e.g. lithium) and $Ar^1$ is as hereinbefore defined; or (c) when X represents $S(O)_n$ and R represents —$C(R^4)(R^5)Ar^1$ where $R^4$ is a $C_{1-4}$ alkyl group, $R^5$ is a hydroxyl group and $Ar^1$ is attached through a carbon atom to —$C(R^4)(R^5)$, reacting a compound of general formula

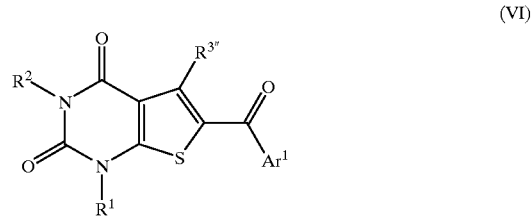

(VI)

wherein $R^{3''}$ represents S—R or S—$Ar^2$ and $R^1$, $R^2$, $R^9$, $Ar^1$ and $Ar^2$ are as hereinbefore defined, with a compound of general formula (VII), $R^{4'}$—MgHal, wherein $R^{4'}$ represents a $C_{1-4}$ alkyl group and Hal represents a halogen atom, optionally followed by an oxidation reaction; or (d) when X represents $SO_2NR^{10}$, reacting a corresponding compound of formula (I) in which $R^3$ represents a hydrogen atom, with sulphur dioxide in the presence of a base, followed by an oxidation step and then reaction with a compound of general formula (VIII), $HNR^{10}R^{17}$, where $R^{17}$ represents a group $R^9$ or $Ar^2$ and $R^9$, $R^{10}$ and $Ar^2$ are as hereinbefore defined; or (e) when R represents —$C(R^4)(R^5)Ar^1$ where $R^5$ represents a hydrogen atom, reacting a corresponding compound of formula (I) in which $R^5$ represents a hydroxyl group, with a reducing agent; or (f) when R represents —$C(R^4)(R^5)Ar^1$ where $R^4$ is a hydrogen atom or a $C_{1-4}$ alkyl group, $R^5$ is a hydrogen atom and $Ar^1$ is attached through a nitrogen heteroatom to —$C(R^4)(R^5)$, reacting a compound of general formula

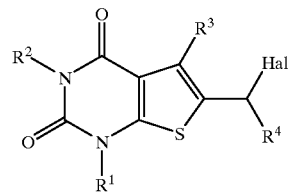

(IX)

wherein Hal represents a halogen atom and $R^1$, $R^2$, $R^3$ and $R^4$ are as hereinbefore defined, with a compound of general formula (X), $Ar^1$—H, wherein $Ar^1$ is as defined above, in the presence of a base; or (g) when R represents a group —$C(O)Ar^1$, oxidising a corresponding compound of formula (I) in which $R^4$ is a hydrogen atom and $R^5$ is a hydroxyl group (e.g. using manganese dioxide at ambient temperature); or (h) when $R^3$ represents a hydrogen atom or a group X—$R^9$ or X—$Ar^2$ where X represents $C(O)NR^{10}$, $C(O)O$, $NH(CO)NR^{10}$ or $NH(CO)O$ and R represents a group —$C(O)Ar^1$, reacting a compound of formula (II) as defined above, with a compound of general formula (XI), $Ar^1CON(CH_3)OCH_3$ wherein $Ar^1$ is as previously defined, in the presence of a base; or (j) when X represents an oxygen atom and R represents a group —$C(O)Ar^1$, reacting a compound of general formula

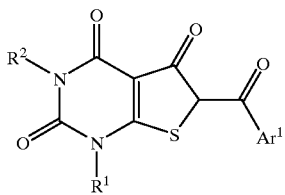

(XII)

wherein $R^1$, $R^2$ and $Ar^1$ are as hereinbefore defined, with a compound of general formula (XIII), $R^{17}$—L, wherein L represents a leaving group (e.g. a halogen atom) and $R^{17}$ is as defined in (d) above; or (k) when X represents an oxygen atom and R represents a group —$CH_2Ar^1$, reacting a compound of general formula

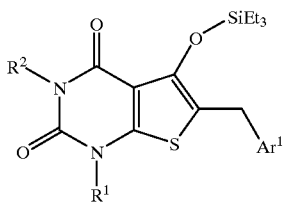

(XIV)

with a compound of formula (XIII) as defined in (j) above;

and optionally after (a), (b), (c), (d), (e), (f), (g), (h), (j) or (k) converting the compound of formula (I) to a further compound of formula (I) and, if desired, forming a pharmaceutically acceptable salt or solvate thereof.

Process step (a) may conveniently be carried out in an organic solvent, e.g. tetrahydrofuran, in the presence of lithium diisopropylamide at a temperature in the range from −78° C. to 50° C.

Process step (b) may conveniently be carried out in an organic solvent, e.g. tetrahydrofuran, at a temperature in the range from −78° C. to ambient conditions.

In process step (c), the reaction between the compounds of formulae (VI) and (VII) is preferably performed in an organic solvent such as tetrahydrofuran at a temperature in the range from −78° C. to ambient conditions. The further optional oxidation reaction to form compounds of formula (I) in which X is SO or $SO_2$ may be carried out by techniques well known to those skilled in the art.

In process step (d), the reaction with sulphur dioxide is conveniently carried out in an organic solvent such as tetrahydrofuran with lithium diisopropylamide as the preferred base, at a temperature of about −78° C. The sulfonic acid intermediate thus formed is conveniently oxidised using N-chlorosuccinimide in the presence of an acid before reaction with the compound of formula (VIII).

Process step (e) is conveniently carried out using triethylsilane/trifluoroacetic acid as the reducing agent under ambient conditions (20° C.).

Process step (f) is very suitably carried out in an organic solvent such as dimethylformamide at ambient temperature. Examples of bases that may be used include sodium hydride and potassium iodide/potassium carbonate.

Process step (g) may conveniently be carried out in an organic solvent such as dichloromethane.

Process step (h) may be carried out in an organic solvent, e.g. tetrahydrofuran, at a temperature in the range from −78° C. to ambient conditions. Suitable bases that may be used include lithium diisopropylamide.

Process step (j) may be carried out in the presence of a base such as sodium hydride in an organic solvent such as tetrahydrofuran or dimethylformamide at ambient temperature.

Process step (k) may be carried out in an organic solvent such as dimethylformamide, and in the presence of tetrabutylammonium fluoride (TBAF).

Compounds of formula (II) in which $R^{3'}$ represents a hydrogen atom or a group X—$R^9$ or X—$A^2$ where X is C(O)O may be prepared by reacting a compound of general formula

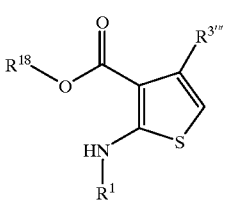

(XV)

wherein $R^{3'''}$ represents a hydrogen atom or a group $CO_2R^9$ or $CO_2Ar^2$, $R^{18}$ represents an alkyl (e.g. ethyl) or aryl group, and $R^1$, $R^9$ and $Ar^2$ are as hereinbefore defined, with a compound of formula

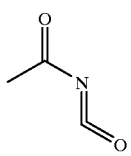

(XVI)

in the presence of a solvent such as toluene, followed by treatment with a base, such as sodium ethoxide in ethanol, and then further reaction with an alkylating agent of general formula (XVII), $R^2$—$L^1$, wherein $L^1$ represents a leaving group such as a halogen atom and $R^2$ is as defined above.

Compounds of formula (XV) in which $R^1$ is a hydrogen atom may be prepared by reacting a compound of general formula (XVI), $CH_3C(O)R^{3'''}$, wherein $R^{3'''}$ is as previously defined, with a compound of general formula

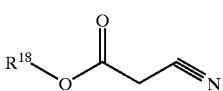

(XIX)

wherein $R^{18}$ is as previously defined, and with elemental sulfur, in a suitable solvent, e.g. dimethylformamide.

Compounds of formula (XV) in which $R^1$ is $CH_2C_{1-5}$ alkyl, $CH_2C_{2-5}$ alkenyl or $CH_2C_{3-5}$cycloalkyl may suitably be prepared by reacting a corresponding compound of formula (XV) in which $R^1$ is H, with a compound of general formula (XX), $R^{19}CO_2H$, wherein $R^{19}$ represents $C_{1-5}$ alkyl, $C_{2-5}$ alkenyl or $C_{3-5}$ cycloalkyl, and with a reducing agent such as sodium borohydride, in the absence of a solvent.

Compounds of formula (XV) in which $R^1$ is $C_{1-6}$ alkyl or $C_{3-6}$ cycloalkyl may conveniently be prepared by reacting a corresponding compound of formula (XV) in which $R^1$ is H, in the presence of a solvent such as toluene and catalytic toluenesulfonic acid under reflux conditions, with a compound of general formula

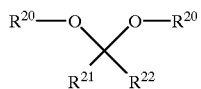
(XXI)

wherein the groups $R^{20}$ are both methyl or ethyl groups, and $R^{21}$ and $R^{22}$ each independently represent a hydrogen atom or an alkyl group or together form a hydrocarbyl ring, the total number of carbon atoms in $R^{21}$ and $R^{22}$ taken together not exceeding five, followed by reaction with a reducing agent such as sodium borohydride.

Compounds of formula (II) in which $R^{3'}$ represents a group $X-R^9$ or $X-Ar^2$ where X is $C(O)NR^{10}$ can be prepared by reacting a compound of general formula

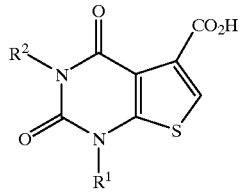
(XXII)

wherein $R^1$ and $R^2$ are as hereinbefore defined, with a compound of formula (VIII) as defined above, in the presence of 1-(3-dimethylaminopropyl)-3-ethylcarbodiimide and 1-hydroxybenzotriazole hydrate.

Compounds of formula (XXII) may be readily prepared by hydrolysing a corresponding compound of formula (I) in which $R^{3'}$ represents a group $CO_2R^9$ in the presence of a base, in a solvent such as aqueous ethanol.

Compounds of formula (II) in which $R^{3'}$ represents a group $X-R^9$ or $X-Ar^2$ where X is $NH(CO)NR^{10}$ may be prepared by reacting a compound of general formula

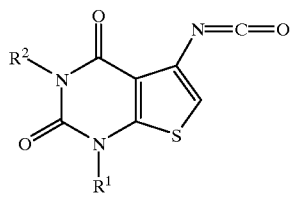
(XXIII)

wherein $R^1$ and $R^2$ are as hereinbefore defined, with a compound of formula (VIII) as described above, in the presence of a solvent such as toluene.

Compounds of formula (XXIII) may be easily prepared by reacting a compound of formula (XXII) as described above with diphenylphosphoryl azide, $(C_6H_5O)_2P(O)N_3$, in the presence of a solvent, e.g. a mixture of triethylamine and toluene.

Compounds of formula (II) in which $R^{3'}$ represents a group $X-R^9$ or $X-Ar^2$ where X is $NH(CO)O$ can be prepared by reacting a compound of formula (XXIII) as defined above, with a compound of general formula (XXIV), $R^{17}OH$, wherein $R^{17}$ is as hereinbefore defined, in the presence of a solvent such as toluene.

The above compounds of formula (II) may be converted into further compounds of formula (II) using conventional techniques.

Compounds of formula (IV) in which $R^3$ represents a hydrogen atom or a group $X-R^9$ or $X-Ar^2$ where X represents $C(O)NR^{10}$, $C(O)O$, $NH(CO)NR^{10}$ or $NH(CO)O$ may be prepared by reacting a compound of formula (II) above with dimethylformamide, in the presence of phosphorus oxychloride ($POCl_3$).

Compounds of formula (IV) in which $R^3$ represents a group $X-R^9$ or $X-Ar^2$ where X is S may be prepared by reacting a compound of general formula

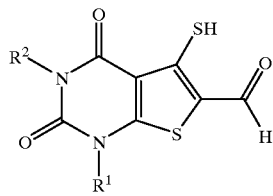
(XXV)

wherein $R^1$ and $R^2$ are as hereinbefore defined, with a compound of general formula (XXVI), $R^{17}-L^2$, wherein $L^2$ represents a leaving group such as a halogen atom and $R^{17}$ is as defined above.

Compounds of formula (XXV) are suitably prepared by reaction of a compound of general formula

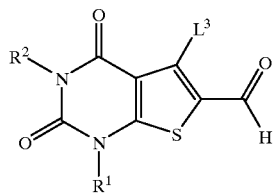
(XXVII)

wherein $L^3$ represents a leaving group such as a halogen atom and $R^1$ and $R^2$ are as hereinbefore defined, with NaSH in aqueous tetrahydrofuran.

Compounds of formula (XXVII) may be prepared by reacting a compound of general formula

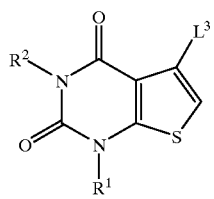
(XXVIII)

wherein $R^1$, $R^2$ and $L^3$ are as hereinbefore defined, with dimethylformamide, in the presence of phosphorus oxychloride ($POCl_3$).

Compounds of formula (XXVIII) in which $L^3$ represents a bromine atom may conveniently be prepared by reacting a compound of general formula

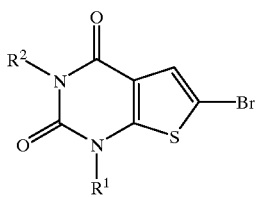

(XXIX)

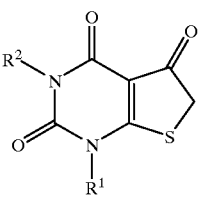

(XXXII)

wherein R¹ and R² are as hereinbefore defined, with a base such as lithium diisopropylamide, followed by protonation of the resulting anion with water.

Alternatively, compounds of formula (IV) in which R³ represents a group X—R⁹ or X—Ar² where X is S may be prepared by reacting a compound of formula (XXVII) as defined above, with a compound of general formula (XXX), R¹⁷—SH, wherein R¹⁷ is as defined above, in the presence of a base, for example, sodium hydride.

Compounds of formula (IV) in which R³ represents a group X—R⁹ or X—Ar² where X is SO₂ may be prepared by oxidising a corresponding compound of formula (IV) where X is S(O)$_n$ and n is 0 or 1, in the presence of an appropriate oxidising agent (e.g. 3-chloroperoxybenzoic acid) and an appropriate solvent (e.g. dichloromethane), for example, at 0° C. to ambient temperature (20° C.).

Compounds of formula (IV) in which R³ represents a group X—R⁹ or X—Ar² where X is SO may be prepared by oxidising a corresponding compound of formula (IV) where X is S, in the presence of an appropriate quantity of a suitable oxidising agent (e.g. potassium peroxymonosulfate, commercially sold under the trade mark "OXONE") in a suitable solvent (e.g. aqueous methanol), for example, at ambient temperature.

Compounds of formula (VI) can be prepared by reacting a compound of formula (XXIX) with a compound of formula (III) wherein R⁴ is a hydrogen atom, in the presence of lithium diisopropylamide, followed by oxidation with tetrapropylammonium perruthenate (TPAP) and N-methylmorpholine N-oxide (NMMO) in a solvent such as dichloromethane and then reaction with a compound of formula (XXX) in the presence of a base such as sodium hydride.

Compounds of formula (IX) in which R³ represents a hydrogen atom or a group X—R⁹ or X—Ar² where X represents C(O)NR¹⁰, C(O)O, NH(CO)NR¹⁰ or NH(CO)O and R⁴ is a hydrogen atom may be prepared by reacting a compound of formula (II) above with formaldehyde in the presence of hydrochloric acid.

Compounds of formula (IX) in which R³ represents a hydrogen atom and R⁴ is a C₁₋₄ alkyl group may be prepared by reacting a compound of formula (II) in which R³' represents a hydrogen atom, with a compound of general formula (XXXI), R⁴ CHO, wherein R⁴' is as previously defined, in the presence of lithium diisopropylamide at −78° C., followed by reaction with a halogenating agent, e.g. a chlorinating agent such as SOCl₂.

Compounds of formula (IX) in which R³ represents a group X—R⁹ or X—Ar² where X is S(O)$_n$ can be prepared by reacting a compound of formula (XXIII) with a compound of formula (XXX), followed by sequential reaction firstly with dimethylformamide, secondly with sodium borohydride or a compound of formula (VII) and thirdly with a halogenating agent, e.g. thionyl chloride, optionally followed by an oxidation reaction.

Compounds of formula (XII) may be prepared by reacting a compound of general formula wherein R¹ and R² are as defined above, with a compound of general formula (XXXIII), L⁴—C(O)Ar¹, wherein L⁴ represents a leaving group such as a halogen, e.g. chlorine, atom and Ar¹ is as defined above, in the presence of a Lewis acid, e.g. aluminium (III) chloride.

Compounds of formula (XIV) may conveniently be prepared from compounds of formula (XXXII) as described in the following reaction scheme:

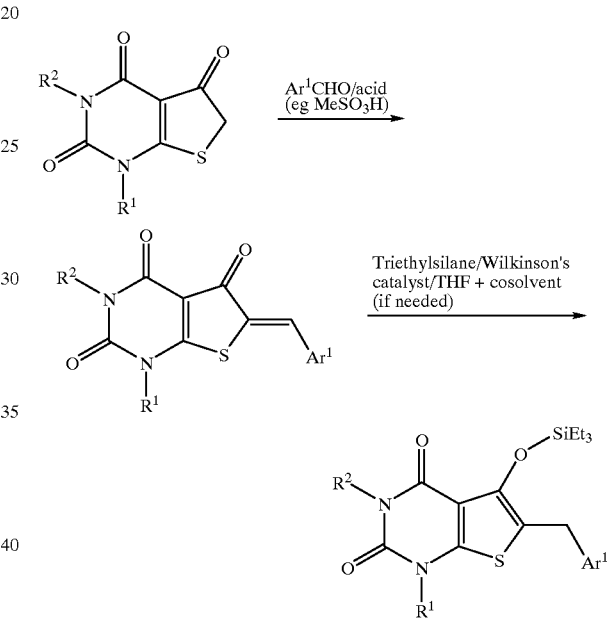

Compounds of formula (I) can be converted into further compounds of formula (I) using standard procedures. For example, compounds of formula (I) where Ar² is nitrophenyl can be converted to compounds of formula (I) where Ar² is aminophenyl by reduction using iron powder and ammonium chloride in ethanol under reflux conditions.

Compounds of formula (M), (V), (VII), (VIII), (X), (XI), (XII), (XVI), (XVII), (XVIII), (XIX), (XX), (XXI), (XXIV), (XXVI), (XXIX), (XXX), (XXXI), (XXXII) and (XXXIII) are either commercially available, are well known in the literature or may be prepared easily using known techniques.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

The compounds of formula (I) above may be converted to a pharmaceutically-acceptable salt or solvate thereof, preferably an acid addition salt such as a hydrochloride, hydrobromide, phosphate, acetate, fumarate, maleate, tartrate, citrate, oxalate, methanesulfonate or p-toluenesulfonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Isomers may be resolved or separated by conventional techniques, e.g. chromatography or fractional crystallisation. Enantiomers may be isolated by separation of a racemic or other mixture of the compounds using conventional techniques (e.g. chiral HPLC). Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of the invention may be isolated from their reaction mixtures using conventional techniques.

The compounds of the invention are useful because they possess pharmacological activity in human and non-human animals. They are therefore indicated as pharmaceuticals for use in the (prophylactic) treatment of autoimmune, inflammatory, proliferative and hyper proliferative diseases and immunologically-mediated diseases including rejection of transplanted organs or tissues and Acquired Immunodeficiency Syndrome (AIDS).

Examples of These Conditions Are:

(1) (the respiratory tract) reversible obstructive airways diseases including asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease.

Accordingly, the present invention provides a compound of formula (I), or a pharmaceutically-acceptable salt or solvate thereof, as hereinbefore defined for use in therapy.

In another aspect, the invention provides the use of a compound of formula (I), or a pharmaceutically-acceptable salt or solvate thereof, as hereinbefore defined in the manufacture of a medicament for use in therapy.

The invention further provides a method of effecting immunosuppression which comprises administering to a patient a therapeutically effective amount of a compound of formula (I), or a pharmaceutically-acceptable salt or solvate thereof, as hereinbefore defined.

The invention still further provides a method of treating, or reducing the risk of, a reversible obstructive airways disease in a patient suffering from, or at risk of, said disease, which comprises administering to the patient a therapeutically effective amount of a compound of formula (I), or a pharmaceutically-acceptable salt or solvate thereof, as hereinbefore defined.

For the above-mentioned therapeutic uses the dosage administered will, of course, vary with the compound employed, the mode of administration, the treatment desired and the disorder indicated. However, in general, for effecting immunosuppression, the daily dosage of the compound of formula (I) will be in the range from 0.1 mg/kg, preferably from 0.3 mg/kg, more preferably from 0.5 mg/kg and still more preferably from 1 mg/kg up to and including 30 mg/kg. For the treatment of obstructive airways diseases, the daily dosage of the compound of formula (I) will typically be in the range from 0.001 mg/kg to 30 mg/kg.

The compounds of formula (I) and pharmaceutically-acceptable salts and solvates thereof may be used on their own but will generally be administered in the form of a pharmaceutical composition in which the formula (I) compound/saltsolvate (active ingredient) is in association with a pharmaceutically-acceptable adjuvant, diluent or carrier. Depending on the mode of administration, the pharmaceutical composition will preferably comprise from 0.05 to 99% w (per cent by weight), more preferably less than 80% w, e.g. from 0.10 to 70% w, and even more preferably less than 50% w, of active ingredient, all percentages by weight being based on total composition.

Thus, the present invention also provides a pharmaceutical composition comprising a compound of formula (I), or a pharmaceutically-acceptable salt or solvate thereof, as hereinbefore defined, in association with a pharmaceutically-acceptable adjuvant, diluent or carrier.

The invention further provides a process for the preparation of a pharmaceutical composition of the invention which comprises mixing a compound of formula (I), or a pharmaceutically-acceptable salt or solvate thereof, as hereinbefore defined, with a pharmaceutically-acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will be illustrated by the subsequent examples in which the following abbreviations are used: m.p.=melting point, NMR=nuclear magnetic resonance, MS=mass spectrometry and h=hour(s).

EXAMPLE 1

(±)-6-[1-Hydroxy-1-(1-methyl-1H-benzinddazol-2-yl)methyl]-3-methyl-1-(2-methylpropyl)thieno[2,3-d]pyrimidine-2,4(1H,3H)-dione

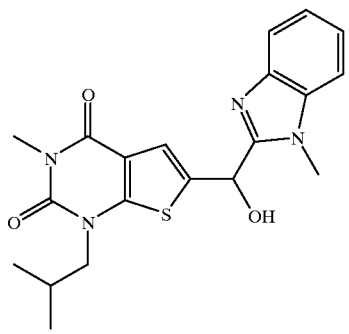

a) 6-Chloro-3-methyl-1-(2-methylpropyl)-1H-pyrimidine-2,4(1H,3H)-dione.

A mixture of 6-chloro-3-methyl-1H-pyrimidine-2,4(1H,3H)-dione (J. Amer. Chem. Soc., 1980, 102, 5036) (27.85 g), 1-iodo-2-methylpropane (21.9 ml) and potassium carbonate (26.36 g) in anhydrous dimethylformamide (110 ml) was stirred at 90° C., under nitrogen for 40 hours. The reaction mixture was cooled to room temperature and diluted with water (800 ml). Brine (100 ml) was added and the mixture was extracted with ether (2×500 ml).

The organic extracts were dried over anhydrous magnesium sulfate, filtered and evaporated under reduced pressure. The residual oil was triturated with ether and the resulting crystals were filtered, washed with ether and dried in vacuo to give the subtitle compound (7.38 g). The mother liquors were evaporated under reduced pressure and purified by column chromatography over silica eluting with isohexane:ether (1:1) to give further subtitle compound (6.90 g).

$^1$H NMR (CDCl$_3$) δ 0.96 (6H, d), 2.10–2.24 (1H, m), 3.34 (3H, s), 3.90 (2H, d), 5.92 (1H, s).

b) 3-Methyl-1-(2-methylpropyl)-6-thioxo-pyrimidine-2,4(1H,3H)-dione

To a stirred solution of 6-chloro-3-methyl-1-(2-methylpropyl)-1H-pyrimidine-2,4(1H,3H)-dione (31.5 g) in ethanol (120 ml) was added sodium hydrogen sulfide hydrate (11.83 g). After 16 hours, further sodium hydrogen sulfide hydrate (5.92 g) was added and stirring was continued for 5 hours. The reaction mixture was diluted with water and was then extracted with ethyl acetate (2×200 ml). The aqueous layer was acidified by addition of concentrated hydrochloric acid and extracted with ethyl acetate (3×500 ml). The combined organic extracts were dried over anhydrous magnesium sulfate, filtered and evaporated under reduced pressure to give the subtitle compound as a solid (25.44 g).

MS (+ve APCI) 215 ((M+H)$^+$); $^1$H NMR (CDCl$_3$) δ 0.94 (6H, d) 2.23–2.38 (1H, m), 3.32 (3H, s), 4.16 (2H, s), 4.30 (2H, d).

c) 3-Methyl-1-(2-methylpropyl)thieno[2,3-d]pyrimidin-2,4 (1H,3H)-dione.

Sodium acetate (38.9 g) was added to a stirred suspension of 3-methyl-1-(2-methylpropyl)-6-thioxo-pyrimidine-2,4 (1H,3H)-dione (25.42 g) in water (1l). After 5 hours, the mixture was filtered. Aqueous chloroacetaldehyde solution (50 wt. %, 142 ml) was added to the filtrate and the mixture was stirred for 16 hours. The mixture was acidified with concentrated hydrochloric acid and extracted with ethyl acetate (3×500 ml). The combined organic extracts were washed with saturated sodium hydrogen carbonate solution, dried over anhydrous magnesium sulfate, filtered and evaporated under reduced pressure. The residual oil was purified by column chromatography over silica, eluting with isohexane:ether (1:1) to give the subtitle compound (26.78 g) as a solid.

MS (+ve APCI) 239 ((M+H)$^+$); $^1$H NMR (CDCl$_3$) δ 1.00 (6H, d), 2.26–2.42 (1H, m), 3.43 (3H, s), 3.81 (2H, d), 6.84 (1 h, d), 7.36 (1H, d).

d) (±)-6-[1-Hydroxy-1-(1-methyl-1H-benzimidazol-2-yl)methyl]-3-methyl-1-(2-methylpropyl)thieno[2,3-d]pyrimidine-2,4(1H,3H)-dione A solution of lithium diisopropylamide (3.15 mmol) in anhydrous tetrahydrofuran (5 ml) was added to a solution of 3-methyl-1-(2-methylpropyl)thieno[2,3-d]pyrimidine-2,4 (1H,3H)-dione (500 mg) in anhydrous tetrahydrofuran (20 ml) at −78° C. After 10 minutes, 1-methylbenzimidazole-2-carboxaldehyde (600 mg) was added and the resultant solution kept at −78° C. for 1 hour. The reaction mixture was allowed to warm to ambient temperature and quenched with saturated sodium hydrogen carbonate solution. The mixture was extracted with ethyl acetate and washed with saturated sodium hydrogen carbonate and then brine, then dried over a mixture of magnesium sulfate and silica, filtered, and evaporated. Purification by HPLC over silica eluting with an isohexane:ethyl acetate gradient (4:1 to 0:1) gave the title compound (0.13 g).

MS (APCI) ((M+H)$^+$) 399; $^1$H NMR (CDCl$_3$) δ 0.94 (6H, dd); 2.25–2.35 (1H, m); 3.39 (3H, s); 3.60–3.90 (2H, m); 370 (3H, s); 6.19 (1H, s); 7.18 (1H, s); 7.30–7.33 (3H, m); 7.77 (1H, dd).

EXAMPLE 2

3-Methyl-6-[(1-methyl-1H-benzimidazol-2-yl)methyll-1-(2-methylpropyl)thieno[2,3-d]pyrimnidine-2,4(1H,3H)-dione

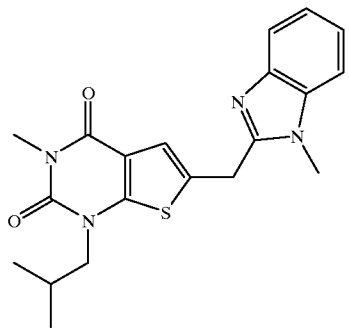

(±)-6-[1-Hydroxy-1-(1-methyl-1H-benzimidazol-2-yl) methyl]-3-methyl-1-(2-methylpropyl)thieno[2,3-d]

pyrimidine-2,4(1H,3H)-dione (100 mg) was dissolved in trifluoroacetic acid (4 ml) and triethylsilane (3 ml) was added. After 6 days the reaction mixture was quenched with 2M sodium hydroxide and extracted with ethyl acetate. The organic phase was washed with 2M sodium hydroxide and then brine, then dried over a mixture of magnesium sulfate and silica, filtered, and evaporated. Purification by column chromatography over silica eluting with ethyl acetate followed by recrystallisation from isohexane:ethyl acetate (4:1) gave the title compound (35 mg).

m.p. 167–169° C.; MS (+ve APCI) ((M+H)$^+$) 383; $^1$H NMR (DMSO d6) δ 0.89 (6H, d), 2.10–2.20 (1H, m), 3.23 (3H, s), 3.70 (2H, d), 3.78 (3H, s), 4.53 (2H, s), 7.15–7.25 (3H, m), 7.50 (1H, d), 7.60 (1H, d).

The compounds of Examples 3 to 10 were prepared from 3-methyl-1-(2-methylpropyl)thieno[2,3-d]pyrimidine-2,4 (1H,3H)-dione (Example 1, step c) and the appropriate aldehyde following the method of Example 1. The compounds of Examples 11 to 17 were prepared from the corresponding alcohol following the method of Example 2:

| Example | Name | m.p. | MS | $^1$H NMR |
|---|---|---|---|---|
| 3 | (±)-6-[1-Hydroxy-1-(2-pyridinyl)methyl]-3-methyl-1-(2-methylpropyl)thieno[2,3-d]-pyrimidine-2,4(1H, 3H)-dione | | (+ve APCI) ((M+H)$^+$) 346 | (CDCl$_3$)δ 0.95(6H, dd), 2.25–2.35(1H, m), 3.40(3H, s), 3.65–3.85(2H, m), 5.45(1H, d), 5.92(1H, d), 7.22(1H, s), 7.25–7.32(2H, m), 7.73(1H, dt), 8.59(1H, d). |
| 4 | (±)-6-[1-Hydroxy-1-(3-pyridinyl)methyl]-3-methyl-1-(2-methylpropyl)thieno[2,3-d]-pyrimidine-2,4(1H, 3H)-dione | | (+ve APCI) ((M+H)$^+$) 346 | (CDCl$_3$)δ 0.97(6H, d), 2.25–2.35(1H, m), 3.40(3H, s), 3.75–3.80(2H, m), 6.04(1H, s), 7.08(1H, s), 7.35(1H, dd), 7.79(1H, d), 8.60(1H, d), 8.68(1H, s). |
| 5 | (±)-6-[1-Hydroxy-1-(4-pyridinyl)methyl]-3-methyl-1-(2-methylpropyl)thieno[2,3-d]-pyrimidine-2,4(1H, 3H)-dione | 148–151° C. | (+ve APCI) ((M+H)$^+$) 346 | (DMSO d6)δ 0.88(6H, dd), 2.10–2.20(1H, m), 3.22(3H, s), 3.60–3.80(2H, m), 6.00(1H, d), 6.75(1H, d), 7.11(1H, s), 7.45(2H, d), 8.55(2H, d). |
| 6 | (±)-6-[1-Hydroxy-1-(2-thienyl)methyl]-3-methyl-1-(2-methylpropyl)thieno[2,3-d]-pyrimidine-2,4(1H, 3H)-dione | | (+ve APCI) ((M+H)$^+$) 351 | (CDCl$_3$)δ 0.99(6H, dd), 2.25–2.35(1H, m), 2.70(1H, d), 3.41(3H, s), 3.70–3.85(2H, m), 6.24(1H, d), 7.00(1H, dd), 7.07(1H, d), 7.18(1H, s), 7.35(1H, d). |

-continued

| Example | Name | m.p. | MS | ¹H NMR |
|---|---|---|---|---|
| 7 | (±)-6-[1-(5-Chloro-2-thienyl)-1-hydroxymethyl]-3-methyl-1-(2-methylpropyl)thieno[2,3-d]pyrimidine-2,4(1H, 3H)-dione | 126–128° C. | (+ve APCI) ((M+H)⁺) 385/387 | (DMSO d6)δ 0.90(6H, d), 2.15–2.25(1H, m), 3.22(3H, s), 3.60–3.80(2H, m), 6.15(1H, d), 6.88(1H, d), 6.99(1H, d), 7.01(1H, d), 7.12(1H, s). |
| 8 | (±)-6-[1-Hydroxy-1-(3-thienyl)methyl]-3-methyl-1-(2-methylpropyl)thieno[2,3-d]-pyrimidine-2,4(1H,3H)-dione | | (+ve APCI) ((M+H)⁺) 351 | (CDCl₃)δ 1.00(6H, d), 2.25–2.35(1H, m), 2.51(1H, d), 3.40(3H, s), 3.70–3.85(2H, m), 6.07(1H, d), 7.05–7.10(1H, m), 7.11(1H, s), 7.30–7.40(2H, m). |
| 9 | (±)-6-[1-Hydroxy-1-(2-thiazolyl)methyl]-3-methyl-1-(2-methylpropyl)thieno[2,3-d]pyrimidine-2,4(1H,3H)-dione | | (+ve APCI) ((M+H)⁺) 352 | (CDCl₃)δ 0.98(6H, d), 2.25–2.35(1H, m), 3.41(3H, s), 3.70–3.85(2H, m), 6.25(1H, br), 7.35(1H, s), 7.41(1H, d), 7.80(1H, d). |
| 10 | (±)-6-[1-(4-Chloro-1-methyl-1H-pyrazol-3-yl)-1-hydroxymethyl]-3-methyl-1-(2-methylpropyl)thieno[2,3-d]pyrimidine-2,4(1H, 3H)-dione | | (+ve APCI) ((M+H—H₂O)⁺) 365/367 | (CDCl₃)δ 0.98(6H, d), 2.30–2.38(1H, m), 3.16(1H, d), 3.40(3H, s), 3.70–3.90(2H, m), 3.89(3H, s), 6.01(1H, d), 7.10(1H, s), 7.38(1H, s). |
| 11 | 3-Methyl-1-(2-methylpropyl)-6-(2-pyridinylmethyl)thieno[2,3-d]pyrimidine-2,4(1H,3H)-dione | 104–5° C. | (+ve APCI) ((M+H)⁺) 330 | (DMSO d6)δ 0.89(6H, d), 2.15–2.25(1H, m), 3.22(3H, s), 3.69(2H, d), 4.26(2H, s), 7.10(1H, s), 7.27(1H, dd), 7.40(1H, d), 7.76(1H, td), 8.54(1H, d). |

-continued

| Example | | Name | m.p. | MS | ¹H NMR |
|---|---|---|---|---|---|
| 12 | 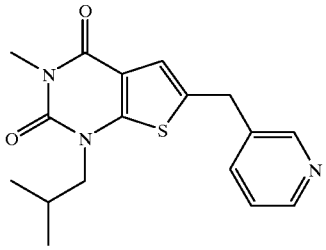 | 3-Methyl-1-(2-methylpropyl)-6-(3-pyridinylmethyl)thieno[2,3-d]pyrimidine-2,4(1H, 3H)-dione | 105–8° C. | (+ve APCI) ((M+H)⁺) 330 | (DMSO d6)δ 0.88(6H, d), 2.10–2.20(1H, m), 3.22(3H, s), 3.67(2H, d), 4.18(2H, s), 7.10(1H, s), 7.38(1H, dd), 7.73(1H, d), 8.46(1H, d), 8.56(1H, s). |
| 13 | 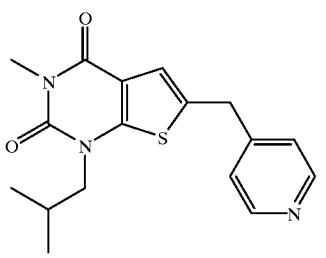 | 3-Methyl-1-(2-methylpropyl)-6-(4-pyridinylmethyl)thieno[2,3-d]pyrimidine-2,4(1H, 3H)-dione | | (+ve APCI) ((M+H)⁺) 330 | (DMSO d6)δ 0.88(6H, d), 2.10–2.20(1H, m), 3.23(3H, s), 3.68(2H, d), 4.18(2H, s), 7.14(1H, s), 7.32(2H, d), 8.50(2H,d). |
| 14 | 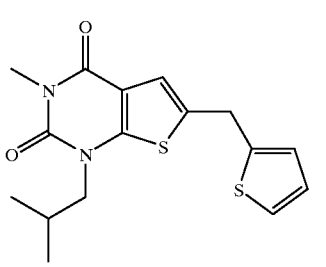 | 3-Methyl-1-(2-methylpropyl)-6-(2-thienylmethyl)thieno[2,3-d]pyrimidine-2,4(1H, 3H)-dione | 75–79° C. | (+ve APCI) ((M+H)⁺) 335 | (DMSO d6)δ 0.89(6H, d), 2.15–2.25(1H, m), 3.23(3H, s), 3.68(2H, d), 4.37(2H, s), 6.97–7.00(2H, m), 7.10(1H, s), 7.40(1H, d). |
| 15 | 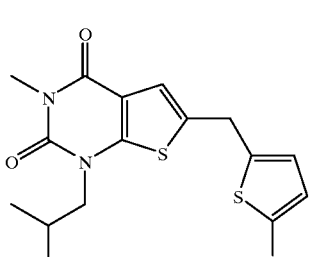 | 6-(5-Chloro-2-thienylmethyl)-3-methyl-1-(2-methylpropyl)thieno[2,3-d]pyrimidine-2,4(1H, 3H)-dione | 128–130° C. | (+ve APCI) ((M+H)⁺) 369/371 | (DMSO d6)δ 0.89(6H, d), 2.10–2.20(1H, m), 3.23(3H, s), 3.69(2H, d), 4.33(2H, s), 6.88(1H, d), 6.98(1H, d), 7.12(1H, s). |
| 16 | 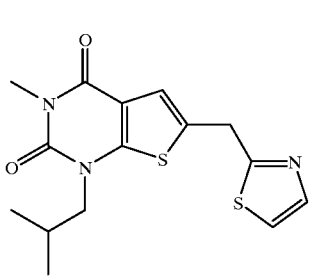 | 3-Methyl-1-(2-methylpropyl)-6-(2-thiazolylmethyl)thieno[2,3-d]pyrimidine-2,4(1H, 3H)-dione | 155–158° C. | (+ve APCI) ((M+H)⁺) 336 | (DMSO d6)δ 0.90(6H, d), 2.15–2.25(1H, m), 3.23(3H, s), 3.70(2H, d), 4.59(2H, s), 7.19(1H, s), 7.65(1H, d), 7.77(1H, d). |

| Example | Name | m.p. | MS | ¹H NMR |
|---|---|---|---|---|
| 17 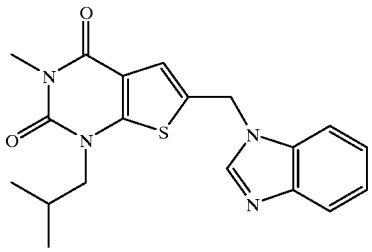 | 6-[(4-Chloro-1-methyl-1H-pyrazol-3-yl)methyl]-3-methyl-1-(2-methylpropyl)thieno[2,3-d]pyrimidine-2,4(1H, 3H)-dione | 144–146° C. | (+ve APCI) ((M+H)⁺) 367/369 | (DMSO d6)δ 0.88(6H, d), 2.10–2.20(1H, m), 3.22(3H, s), 3.68(2H, d), 3.79(3H, s), 4.06(2H, s), 6.99(1H, s), 7.91(1H, s). |

EXAMPLE 18

6-[(1H-Benzimidazol-1-yl)methyl]-3-methyl-1-(2-methylpropyl)thieno(2,3-d]pyridine-2,4(1H,3H)-dione a) 6-Chloromethyl-3-methyl-1-(2-methylpropyl)thieno[2,3-d]pyrimidine-2,4(1H,3H)-dione 37% formaldehyde solution (0.5 ml) was added dropwise to a suspension of 3-methyl-1-(2-methylpropyl)thieno[2,3-d]pyrimidine-2,4(1H,3H)-dione (Example 1 step c; 1.0 g) in concentrated hydrochloric acid (1 ml) at 0° C. After 1.5 h the reaction mixture was warmed to to ambient temperature and stirred overnight. The reaction mixture was diluted with 2M sodium hydroxide solution and extracted with ethyl acetate. The organic phase was washed with 2M sodium hydroxide solution and brine, then dried over magnesium sulfate and evaporated in vacuo. Purification by column chromatography over silica eluting with isohexane:ethyl acetate (7:3 to 1:1) gave the subtitle compound (740 mg).

MS (EI) 286/288 (M⁺); ¹H NMR (DMSO d6) δ 0.93 (6H, d), 2.15–2.25 (1H, m), 3.23 (3H, s), 3.74 (2H, d), 5.06 (2H, s), 7.38 (1H, s).

b) 6-[(1H-Benzimidazol-1-yl)methyl]-3-methyl-1-(2-methylpropyl)thieno[2,3-d]pyrimidine-2,4(1H,3H)-dione Potassium iodide (few crystals), potassium carbonate (140 mg) and benzimidazole (100 mg) were added to a solution of 6-chloromethyl-3-methyl-1-(2-methylpropyl)thieno[2,3-d]pyrimidine-2,4(1H,3H)-dione (170 mg) in dimethylformamide (5 ml). After 2 h the reaction mixture was diluted with ethyl acetate and washed with saturated sodium hydrogen carbonate solution thrice and with brine, then dried over magnesium sulfate and evaporated. Column chromatography of the residue eluting with isohexane:ethyl acetate (1:1 to 0:1) containing 1% Et₃N gave the title compound (130 mg).

m.p. 198–199° C.; MS (+ve APCI) ((M+H)⁺) 369; ¹H NMR (DMSO d6) δ 0.86 (6H, d), 2.07–2.19 (1H, m), 3.21 (3H, s), 3.64 (2H, d), 5.71 (2H, s), 7.18–7.30 (2H, m), 7.49 (1H, s), 7.64 (H, d), 7.66 (1H, d), 8.41 (1H,s).

The following compounds were prepared from 6-chloromethyl-3-methyl-1-(2-methylpropyl)thieno[2,3-d]pyrimidine-2,4(1H,3H)-dione (Example 18 step a) and the appropriate heterocycle, following the method of Example 18 step b:

| Example | Name | m.p. | MS | ¹H NMR |
|---|---|---|---|---|
| 19 | 6-(2H-Benzotriazol-2-ylmethyl)-3-methyl-1-(2-methylpropyl)-thieno[2,3-d]-pyrimidine-2,4(1H, 3H)-dione | 187° C. | | (DMSO d6)δ 0.89(6H, dd), 2.10–2.20(1H, m), 3.22(3H, s), 3.69(2H, d), 6.22(2H, s), 7.40–7.50 (2H, m), 7.51(1H, s), 7.90–8.00(2H, m). |

| Example | Name | m.p. | MS | ¹H NMR |
|---|---|---|---|---|
| 20 | 6-(1H-Benzotriazol-1-ylmethyl)-3-methyl-1-(2-methylpropyl)thieno[2,3-d]-pyrimidine-2,4(1H, 3H)-dione | 169° C. | | (DMSO d6)δ 0.85(6H, d), 2.05–2.15(1H, m), 3.21(3H, s), 3.65(2H, d), 6.20(2H, s), 7.42(1H, t), 7.55(1H, s), 7.59(1H, t), 8.02(1H, d), 8.06(1H, d). |
| 21 | 6-(2H-Indazol-2-ylmethyl)-3-methyl-1-(2-methylpropyl)thieno[2,3-d]-pyrimidine-2,4(1H, 3H)-dione | | | (CDCl₃)δ 0.95(6H, d), 2.22–2.32(1H, m), 3.40(3H, s), 3.72(2H, d), 5.68(2H, s), 7.10(1H, t), 7.31(1H, t), 7.33(1H, s), 7.65(1H, d), 7.73(1H, d), 7.99(1H, s). |
| 22 | 6-(1H-Indazol-1-ylmethyl)-3-methyl-1-(2-methylpropyl)thieno[2,3-d]-pyrimidine-2,4(1H, 3H)-dione | 120° C. | | (DMSO d-6)δ 0.86(6H, d), 2.07–2.17(1H, m), 3.20(3H, s), 3.64(2H, d), 5.85(2H, s), 7.15(1H, t), 7.39(1H, s), 7.42(1H, t), 7.77(1H, d), 7.85(1H, d), 8.15(1H, s). |
| 23 | 3-Methyl-1-(2-methylpropyl)-6-[(1H-pyrrolo[2,3-b]pyridin-3-yl)methyl]thieno[2,3-d]-pyrimidine-2,4-1H, 3H)-dione | 216° C. | 369 ((M+H)⁺) | (DMSO d6)δ 0.85(6H, d), 2.10–2.15(1H, m), 3.22(3H, s), 3.63(2H, d), 4.25(2H, s), 7.02(1H, dd), 7.11(1H, s), 7.43(1H, s), 7.88(1H, d), 8.20(1H, d), 11.50(1H, br s) |

EXAMPLE 24

(±)-6-[1-Hydroxy-1-(benzothiazol-2-yl)methyl]-3-methyl-1-(2-methylpropyl)thieno[2,3-d]pyrimidine-2,4(1H,3H)-dione

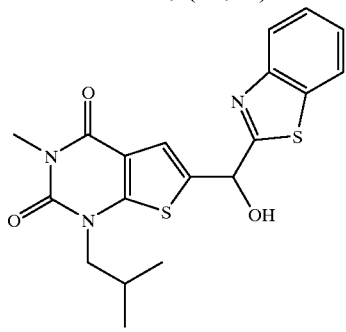

a) 1,2,3,4-tetrahydro-3-methyl-1-(2-methylpropyl)-2,4-dioxothieno[2,3-d]pyrimidine-6-carboxaldehyde 1,2,3,4-tetrahydro-3-methyl-1-(2-methylpropyl)-2,4-dioxothieno[2,3-d]pyrimidine-6-carboxaldehyde (300 mg) was dissolved in phosphorus oxychloride (4 ml) and dimethylformamide (2 ml) added. The mixture was then heated to 100° C. with stirring under nitrogen for 1 hour. The mixture was allowed to cool to ambient temperature and then added dropwise to hot water (–50° C.), containing a small amount of 2M hydrochloric acid, with vigorous stirring. The mixture formed was allowed to cool to ambient temperature and filtered to give the title compound as a brown solid (210 mg).

MS (+ve APCI) ((M+H)⁺) (APCI) 266; ¹H NMR (CDCl₃) δ 1.01 (6H, d); 2.34 (1H, m); 3.44 (3H, s); 3.84 (2H, d); 8.04 (1H, s); 9.85 (1H, s).

b) (±)-6-[1-Hydroxy-1-(benzothiazol-2-yl)methyl]-3-methyl-1-(2-methylpropyl)thieno[2,3-d]pyrimidine-2,4(1H, 3H)-dione Lithium diisopropylamide (2.25 mmol) was added to a solution of benzothiazole (230 mg) in tetrahydrofuran (10 ml) at −78° C. After 5 minutes 1,2,3,4-tetrahydro-3-methyl-1-(2-methylpropyl)-2,4-dioxothieno[2,3-d]pyrimidine-6-carboxaldehyde (300 mg) was added and the reaction mixture kept at −78° C. After a further 30 minutes saturated sodium hydrogen carbonate solution was added and the reaction mixture was allowed to warm to room temperature. The mixture was extracted with ethyl acetate, dried over magnesium sulfate and evaporated. Purification by chromatography eluting with isohexane:ethyl acetate (2:1 to 1:2) gave the title compound as an oil (150 mg).

MS (+ve APCI) ((M+H−H20)$^+$) 384; $^1$H NMR (CDCl$_3$) δ 0.96 (6H, dd), 2.27–2.34 (1H, m), 3.41 (3H, s), 3.75 (2H, dq), 408 (1H, d), 6.32 (1H, d), 7.41 (1H, s), 7.43 (1H, t), 7.52 (1H, t), 7.89 (1H, d), 8.05 (1H, d).

EXAMPLE 25

6-(Benzothiazol-2-yl)methyl-3-methyl-1-(2-methylpropyl)thieno[2,3-d]pyrimidine-2,4(1H,3H)-dione

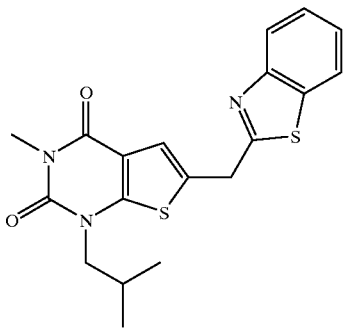

Prepared from (±)-6-[1-hydroxy-1-(benzothiazol-2-yl)methyl]-3-methyl-1-(2-methylpropyl)thieno[2,3-d]pyrimidine-2,4(1H,3H)-dione following the method of Example 2.

mp 104–107° C.; MS (+ve APCI) ((M+H)$^+$) 386; $^1$H NMR (DMSO d6) δ 0.90 (6H, d), 2.15–2.20 (1H, m), 3.24 (3H, s), 3.70 (2H, d), 4.73 (2H, s), 7.30 (1H, s), 7.43 (1H, t), 7.51 (1H, t), 7.97 (1H, d), 8.06 (1H, d).

EXAMPLE 26

6-[1-Hydroxy-1-(1-methyl-1H-benzimidazol-2-yl)methyl]-3-methyl-1-(1-methylethyl)thienof2,3-d]pyrinidine-2,4(1H, 3H)-dione

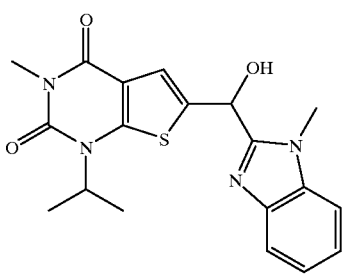

a) Ethyl 2-(1-methylethyl)amninothiophene-3-carboxylate
p-Toluenesulfonic acid (1 g) was added to a stirred solution of 2-amino-3-ethoxycarbonylthiophene (*Chem. Ber.* 1965, 98, 3571; ca.98 g) and 2,2-dimethoxypropane (158 ml) in anhydrous toluene (650 ml) and the mixture was heated at reflux for 5 h. The solution was cooled to room temperature and then added to saturated sodium hydrogen carbonate solution (11) and extracted with ether (11). The organic extracts were dried over anhydrous sodium sulfate, filtered and evaporated. The residual oil was dissolved in ethanol (250 ml) and sodium borohydride (8 g) was added. The mixture was stirred for 3 days and then more sodium borohydride (8 g) was added, then stirred for a further 1 day and to then another portion of sodium borohydride (4 g) was added. After a further 2 days, water (100 ml) followed by saturated sodium hydrogen carbonate solution (750 ml) was added and the mixture was extracted with ether (2×750 ml). The organic extracts were dried over anhydrous magnesium sulfate, filtered and evaporated. The residue was purified by column chromatography over silica, eluting with hexane/dichloromethane (1:1) to give the subtitle compound (24.65 g) as an oil.

MS (+ve APCI) 214 ((M+H)$^+$); $^1$H NMR (CDCl$_3$) δ 1.31 (6H, d), 1.33 (3H, t), 3.47–3.53 (1H, m), 4.25 (2H, q), 6.15 (1H, d), 7.02 (1H, d), 7.36 (1H, s, br).

b) 3-Methyl-1-(1-methylethyl)thieno[2,3-d]pyrimidine-2,4 (1H, 3H)-dione

Acetyl chloride (9.84 ml) was added to a stirred suspension of silver cyanate (21.6 g) in anhydrous toluene (100 ml) under nitrogen. After 30 minutes, a solution of 2-(1-methylethyl)amino-3-ethoxycarbonylthiophene (24.6 g) in anhydrous toluene (20 ml) was added. After a further 2 hours, ether (500 ml) was added and the mixture was filtered and then washed with saturated sodium hydrogen carbonate solution (200 ml). The aqueous layer was extracted with ether (200 ml). The combined organic extracts were dried over anhydrous magnesium sulfate, filtered and evaporated. The residual oil was dissolved in ethanol (150 ml) and sodium ethoxide (23.6 g) was added. The mixture was stirred at room temperature for 3 days and then iodomethane (21.5 ml) was added and the mixture heated under reflux for 3 hours. Further iodomethane (10 ml) was added and heating continued for 1 hour. The reaction mixture was cooled to room temperature and then added to saturated sodium hydrogen carbonate solution (11) and extracted with ether (2×500 ml). The combined organic extracts were dried over anhydrous magnesium sulfate, filtered and evaporated. The residue was purified by column chromatography over silica, eluting with isohexane:ether (1:1) to give the subtitle compound (15.8 g).

MS (+ve APCI) 225 ((M+H)$^+$); $^1$H NMR (CDCl$_3$) δ 1.61 (6H, d), 3.41 (3H, s), 4.65–4.80 (1H, m), 6.85 (1H, d), 7.37 (1H, d).

c) 6-[1-Hydroxy-1-(1-methyl-1H-benzimidazol-2-yl)methyl]-3-methyl-1-(1-methylethyl)thieno[2,3-d]pyrimidine-2,4(1H, 3H)-dione Prepared from 3-Methyl-1-(1-methylethyl)thieno[2,3-d]pyrimidine-2,4(1H, 3H)-dione and 2-formyl-1-methylbenzimidazole following the method of Example 1 step d.

MS (+ve APCI) 385 ((M+H)$^+$).

EXAMPLE 27

3-Methyl-6-[(1-methyl-1H-benzimidazol-2-yl)methyl]-1-(1-methylethyl)thieno[2,3-d]pyrimidine-2,4(1H, 3H)-dione

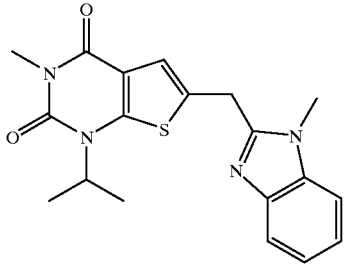

Prepared from 6-[1-Hydroxy-1-(1-methyl-1H-benzimidazol-2-yl)methyl]-3-methyl-1-(1-methylethyl)thieno[2,3-d]pyrimidine-2,4(1H, 3H)-dione following the method of Example 2.

m.p. 142–143° C.; MS (+ve APCI) 369 ((M+H)$^+$); $^1$H NMR (CDCl$_3$) δ 1.56 (6H, d), 3.38 (3H, s), 3.75 (3H, s), 4.44 (2H, d), 4.50–4.65 (1H, m), 7.19 (1H, t), 7.26–7.36 (3H, m), 7.75–7.79 (1H, m).

EXAMPLE 28

(3R)-1-{[1,2,3,4-Tetrahydro-3-methyl1-(2-methylpropyl)-6-(3-pyridinyl)methyl-2,4-dioxothieno[2,3-d]pyrimidin-5-yl]sulfonyl}pyrrolidin-3-ol

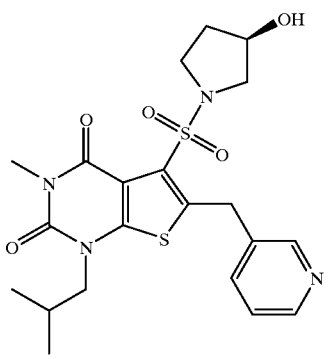

a) 1,2,3,4-Tetrahydro-3-methyl-1-(2-methylpropyl)-6-(3-pyridinyl)methyl-2,4-dioxothieno[2,3-d]pyrimidine-5-sulfonic acid, lithium salt A solution of lithium diisopropylamide (2.74 mmol) in anhydrous tetrahydrofuran (11.3 ml) was added dropwise to a solution of 3-methyl-1-(2-methylpropyl)-6-(3-pyridinyl)methylthieno[2,3-d]pyrimidine-2,4-(1H, 3H)-dione (example 12, 750 mg) in anhydrous tetrahydrofuran (25 ml) at −78° C. under nitrogen. After 10 minutes, a steady stream of sulfur dioxide was passed through the solution for 10 minutes. The mixture was warmed to room temperature, diluted with ether and stirred for 16 hours. The precipitated solid was filtered off to give the crude subtitle compound (525 mg). The liquors were evaporated and the residue triturated with ether. A solid was filtered off to give further crude material (444 mg).

MS (+ve APCI) 394 ((M−Li+2H)$^+$).

b) 1,2,3,4-Tetrahydro-3-methyl-1-(2-methylpropyl)-6-(3-pyridinyl)methyl-2,4-dioxothieno[2,3-d]pyrimidine-5-sulfonyl chloride A solution of 1,2,3,4-tetrahydro-3-methyl-1-(2-methylpropyl)-6-(3-pyridinyl)methyl-2,4-dioxothieno[2,3-d]pyrimidine-5-sulfonic acid lithium salt (crude, 960 mg) in water (100 ml) was filtered through a glass fibre filter and then washed with ether (50 ml). Dichloromethane (60 ml) and N-chlorosuccinimde (200 mg) were added to the aqueous layer and the mixture was stirred vigorously for 2 hours. The organic layer was separated to give a solution of the subtitle compound in dichloromethane (60 ml).

c) 3R)-1-{[1,2,3,4-Tetrahydro-3-methyl-1-(2-methylpropyl)-6-(3-pyridinyl)methyl-2,4-dioxothieno[2,3-d]pyrimidin-5-yl]sulfonyl}pyrrolidin-3-ol (R)-3-Hydroxypyrrolidine (50 mg) was added to the solution of 1,2,3,4-tetrahydro-3-methyl-1-(2-methylpropyl)-6-(3-pyridinyl)methyl-2,4-dioxothieno[2,3-d]pyrimidine-5-sulfonyl chloride (20 ml). After 1 hour, the solution was dried over anhydrous magnesium sulfate and filtered through a small silica pad, washing with ethyl acetate/methanol (19:1). The filtrate was evaporated and the residue was purified by preparative HPLC with dichloromethane:ethanol gradient elution followed by crystallisation from ethyl acetate/isohexane to give the title compound (11 mg).

m.p. 161–162° C.; MS (+ve APCI) 479 ((M+H)$^+$); $^1$H NMR (CDCl$_3$) δ 0.96 (6H, d), 1.98–2.07 (1H, m), 2.17–2.08 (2H, m), 2.39 (1H, d) (3H, s), 3.42–3.47 (2H, m), 3.56 (1H, dd), 3.73 (2H, dd), 3.91 (1H, d), 4.40–4.48 (1H, m), 4.59 (2H, s), 7.29 (1H, dd), 7.65 (1H, dt), 8.54–8.58 (2H, m).

EXAMPLE 29

1-{[1,2,3,4-Tetrahydro-3-methyl-1-(2-methylpropyl)-6-(3-pyridinyl)methyl-2,4-dioxothieno[2,3-d]pyrimnidin-5-yl]sulfonyl}pyrrolidine

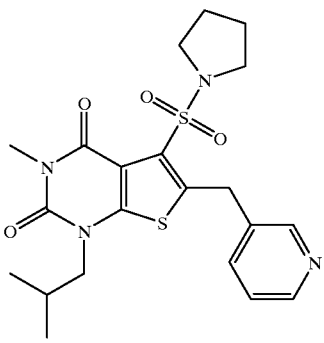

Prepared from pyrrolidine (50 mg) and the dichloromethane solution of 1,2,3,4-tetrahydro-3-methyl-1-(2-methylpropyl)-6-(3-pyridinyl)methyl-2,4-dioxothieno[2,3-d]pyrimidine-5-sulfonyl chloride (Example 28, step b, 20 ml) following the procedure of Example 28 step c to give the title compound (12 mg).

m.p. 133–135° C.; MS (+ve APCI) 463 ((M+H)$^+$); $^1$H NMR (CDCl$_3$) δ 0.95 (6H, d), 1.85–1.90 (4H, m), 2.16–2.28 (1H, m), 3.40 (3H, s) 3.45–3.49 (4H, m), 3.72 (2H, d), 4.58 (2H, s), 7.28 (1H, dd), 7.66 (1H, dt), 8.53–8.57 (2H, m).

EXAMPLE 30

±6-[(1H-Benzimnidazol-2-yl)-1-hydroxymethyl]-3-methyl-1-(2-methylpropyl)thieno[2,3-d]pyriniidine-2,4(1H,3H)-dione

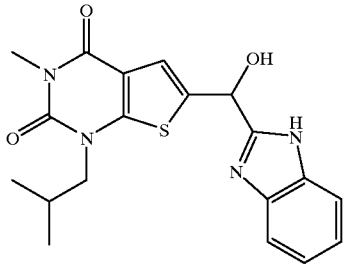

a) 1,2,3,4-tetrahydro-3-methyl-1-(2-methylpropyl)-2,4-dioxothieno[2,3-d]pyrimidine-6-carboxaldehyde 1,2,3,4-tetrahydro-3-methyl-1-(2-methylpropyl)-2,4-dioxothieno[2,3-d]pyrimidine (300 mg; WO98/54190) was dissolved in phosphorus oxychloride (4 ml) and dimethylformamide (2 ml) was added. The mixture was then heated to 100° C. with stirring under nitrogen for 1 hour. The mixture was allowed to cool to ambient temperature and then added dropwise to vigorously stirred hot water (~50° C.), containing a small amount of 2M hydrochloric acid. The mixture formed was allowed to cool to ambient temperature and filtered to give the title compound as a brown solid (210 mg).

MS (APCI) 266 (M+); $^1$H NMR (CDCl$_3$) δ 1.01 (6H, d); 2.34 (1H, m); 3.44 (3H, s); 3.84 (2H, d); 8.04 (1H, s); 9.85 (1H, s)

b) ±6-[(1H-Benzimidazol-2-yl)-1-hydroxymethyl]-3-methyl-1-(2-methylpropyl)thieno[2,3-d]pyrinidine-2,4(1H,3H)-dione Paraformaldehyde (101 mg) and benzimidazole (133 mg) were mixed together in tetrahydrofuran (8 ml). After 24 h the mixture was cooled to −20° C. and n-butyl lithium (2M in hexanes, 1.8 ml) was added. After 30 mins the reaction mixture was cooled to −78° C. and a solution of 3-methyl-1-(2-methylpropyl)-2,4-dioxo-1,2,3,4-tetrahydro-thieno[2,3-d]pyrimidine-6-carboxaldehyde (300 mg) in tetrahydrofuran (8 ml) was added. After 2 h the reaction mixture was allowed to warm to ambient temperature and was then diluted with diethyl ether. The organic solution was extracted thrice with dilute hydrochloric acid. The acid phases were combined, basified with potassium hydroxide and extracted with ethyl acetate. The organic phase was dried over magnesium sulfate and evaporated. Purification by chromatography on silica gel (eluting ethyl acetate/methanol/triethylamine 100:0:1 to 100:5:1) gave the title compound (30 mg).

Melting Point 230–235° C.; MS (APCI) (M+H)+385; $^1$H NMR (DMSO-d$_6$) δ 0.90 (6H, d), 2.15–2.25 (1H, m), 3.23 (3H, s), 3.65–3.80 (2H, m), 6.17 (1H, d), 7.06 (1H, d), 7.10–7.20 (3H, m), 7.46 (1H, dd), 7.57 (1H, dd), 12.50 (1H, brs).

EXAMPLE 31

6-[(1H-Benzimidazol-1-yl)methyl]-3-methyl-1-(1-methylethyl)thieno[2,3-d]pyrimidine-2,4(1H,3H)-dione

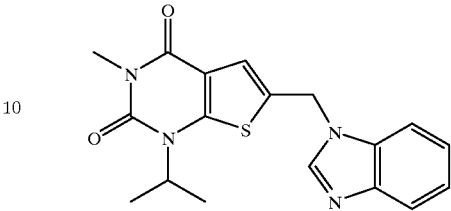

a) Ethyl 2-[(1-methylethyl)amino]thiophene-3-carboxylate

A solution of ethyl 2-aminothiophene-3-carboxylic acid (Chem.Ber.; 1965; 98; 3571–3577, 98.8 g), 4-toluenesulfonic acid (1 g) and 2,2-dimethoxypropane (158 ml) in anhydrous toluene (650 ml) was heated at reflux under nitrogen for 5 hours. The solution was allowed to cool and was then added to saturated aqueous sodium bicarbonate solution (500 ml) and extracted with ether (500 ml). The organic extracts were dried over anhydrous magnesium sulfate, filtered and evaporated. The residual oil was dissolved in ethanol (250 ml) containing sodium borohydride (8 g). The mixture was stirred for 3 days and then further sodium borohydride (8 g) was added. The mixture was stirred for 1 further day, then sodium borohydride (4 g) was added. After a further 2 days stirring, saturated aqueous sodium bicarbonate solution (750 ml) was added and the mixture was extracted with ether (2×750 ml). The organic extracts were dried over anhydrous magnesium sulfate, filtered and evaporated. The residual oil was purified by column chromatography over silica, eluting with dichloromethane/isohexane (1:1) to give the subtitle compound (24.65 g) as an oil.

MS (+ve APCI) 214 ((M+H)+); $^1$H NMR (CDCl$_3$) δ 1.31 (6H, d), 1.33 (3H, t), 3.46–3.54 (1H, m), 4.25 (2H, q), 6.15 (1H, d), 7.02 (1H, d), 7.36 (1H, d, br).

b) 3-Methyl-1-(1-methylethyl)thieno[2,3-d]pyriniidine-2,4(1H,3H)-dione

Acetyl chloride (9.84 ml) was added to a stirred suspension of silver cyanate (21.6 g) in anhydrous toluene (100 ml) under nitrogen. After 30 minutes, a solution of ethyl 2-[(1-methylethyl)amino]thiophene-3-carboxylate (24.6 g) in anhydrous toluene (20 ml) was added. After a further 3 hours, ether (500 ml) was added and the mixture was filtered. The filtrate was washed with saturated aqueous sodium bicarbonate solution (200 ml) and the aqueous layer was extracted with ether (200 ml). The combined organic extracts were dried over anhydrous magnesium sulfate, filtered and evaporated. The residual oil was dissolved in ethanol (150 ml), sodium ethoxide (23.6 g) was added, and the mixture was stirred at room temperature for 3 days. Iodomethane (21.5 ml) was added and the mixture was heated at reflux for 3 hours. Further iodomethane (10 ml) was added and reflux was continued for 1 hour. The mixture was allowed to cool, and was then added to saturated aqueous sodium bicarbonate solution (1 L) and extracted with ether (2×500 ml). The organic extracts were dried over anhydrous magnesium sulfate, filtered and evaporated. The residual oil was purified by column chromatography over silica, eluting with ether/isohexane (1:1) to give the subtitle compound (15.8 g) as a solid.

MS (+ve APCI) 225 ((M+H)+); $^1$H NMR (CDCl$_3$) δ 1.61 (6H, d), 3.41 (3H, s), 4.72 (1H, br), 6.85 (1H, d), 7.37 (1H, d).

c) 6-(Chloromethyl)-3-methyl-1-(1-methylethyl)thieno[2,3-d]pyrimidine-2,4(1H,3H)-dione Aqueous formaldehyde (37%, 2.5 ml) was added to a stirred solution of 3-methyl-1-(1-methylethyl)thieno[2,3-d]pyrimidine-2,4(1H,3H)-dione (1.0 g) in concentrated hydrochloric acid (5 ml) at 0° C. The mixture was saturated with hydrogen chloride gas and stirred at 0° C. for 3 hours and then at room temperature for 3 days. Ethyl acetate (100 ml) was added, the mixture was washed with water (100 ml) and then with saturated aqueous sodium bicarbonate solution (100 ml), then dried over anhydrous magnesium sulfate, filtered and evaporated to give the subtitle compound (1.1 g).

LCMS (+ve APCI) 255 ((M+H)$^+$), for hydrolysis product).

d) 6-[(1H-Benzimidazol-1-yl)methyl]-3-methyl-1-(1-methylethyl)thieno[2,3-d]pyrimidine-2,4(1H,3H)-dione Benzimidazole (0.395 g) and potassium carbonate (1 g) were added to a stirred solution of 6-(chloromethyl)-3-methyl-1-(1-methylethyl)thieno[2,3-d]pyrimidine-2,4(1H,3H)-dione (0.55 g) in anhydrous dimethylformamide (5 ml) at room temperature. After 2 days, water (50 ml) was added and the mixture was extracted with ethyl acetate (2×50 ml). The organic extracts were dried over anhydrous magnesium sulfate and filtered through a silica pad which was washed with ethyl acetate. The filtrate was evaporated and the residue was purified twice by normal-phase preparative HPLC with gradient dichloromethane/ethanol elution to give the title compound (0.394 g) as a foam.

MS (+ve APCI) 355 ((M+H)$^+$); $^1$H NMR (DMSO d$_6$) δ 1.43 (6H, d), 3.19 (3H, s), 4.44 (1H, br), 5.72 (2H, s), 7.21 (1H, t), 7.28 (1H, t), 7.48 (1H, s), 7.66 (1H, d), 7.73 (1H, d), 8.41 (1H, s).

EXAMPLE 32

6-([1H-Benzimidazol-1-yl]methyl)-1-(cyclopropylmethyl)-3-methyl-thieno[2,3-9]pyrimidine-2,4(1H, 3H)-dione

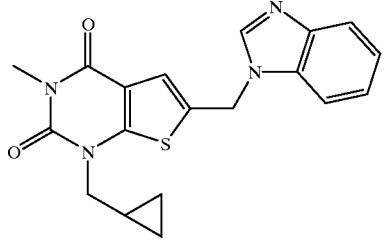

a) 3-Methyl-1-(cyclopropylmethyl)thieno[2,3-d]pyrimidine-2,4(1H,3H)-dione

Potassium carbonate (1.0 g) was added to a mixture of 3-methylthieno[2,3-d]pyrimidine-2,4(1H,3H)-dione (400 mg; J. Chem. Soc. Perkin Trans.1; 1980; 1853) and cyclopropylmethyl bromide (1.0 ml) in dry dimethylformamide (15 ml). The solution was stirred at room temperature for 20 hours and was then diluted with water and extracted thrice with diethyl ether. The combined organic extracts were washed with brine, then dried, filtered and evaporated. The residue was purified by column chromatography over silica, eluting with ethyl acetate: isohexane (1:4) to give the subtitle compound (180 mg).

m.p. 75–7° C.; MS (APCI) 237 ((M+H)$^+$); $^1$H NMR (CDCl$_3$) δ 0.49–0.54 (2H, m); 0.56–0.64 (2H, m); 1.30–1.39 (1H, m); 3.44 (3H,s); 3.90 (2H, d); 6.86 (1H, d); 7.37 (1H, d).

b) 6-(Chloromethyl)-1-(cyclopropylmethyl)3-methylthieno[2,3-d]pyrimidine-2,4(1H,3H)-dione Prepared from 3-methyl-1-(cyclopropylmethyl)thieno[2,3-d]pyrimidine-2,4(1H,3H)-dione following the method of Example 31 step c to give the subtitle compound.

MS (+ve APCI) 267 ((M+H)$^+$) (alcohol derived from hydrolysis of chloro).

c) 6-([1HBenzimidazol-1-yl]methyl)-1-(cyclopropylmethyl)-3-methyl-thieno[2,3-9]pyrimidine-2,4(1H,3H)-dione Prepared from 6-(chloromethyl)-1-(cyclopropylmethyl)-3-methylthieno[2,3-d]pyrimidine-2,4(1H,3H)-dione, benzimidazole and sodium hydride following the method of Example 31 step d to give the title compound.

m.p. 175–176° C.; MS (+ve APCI) 367 ((M+H)$^+$); $^1$H NMR (CDCl$_3$) δ 0.42–0.46 (2H, m), 0.53–0.56 (2H, m),1.20–1.26 (1H, m), 3.41 (3H, s), 3.76–3.79 (2H, m), 5.48 (2H,s), 7.30–7.33 (2H, m), 7.38–7.40 (2H, m), 7.82–7.86 (1H, m), 7.98 (1H, s)

EXAMPLE 33

1-(Cyclopropylmethyl)-6-[1-hydroxy-1-(1-methyl-1Hbenzimidazol-2-yl)methyl]-3-methylthieno[2,3-d]pyrimidin-2,4(1H,3H)-dione

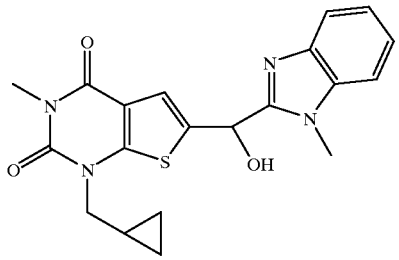

The title compound was prepared from 3-Methyl-1-(cyclopropylmethyl)thieno[2,3-d]pyrimidine-2,4(1H,3H)-dione (Example 32 step a) and 1-methylbenzimidazole-2-carboxaldehyde following the method of Example 1 step d.

MS (+ve APCI) 397 ((M+H)$^+$).

EXAMPLE 34

1-(Cyclopropylmethyl)-6-[(1-methyl-1H-benzinidazol-2-yl)methyl]-3-methylthieno[2,3-d]pyrimidin-2,4(1H,3H)-dione

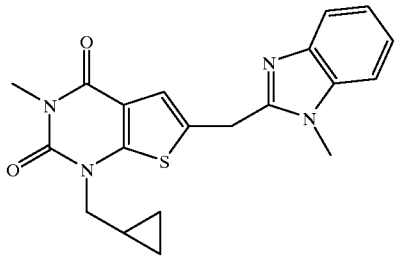

Prepared from 1-(Cyclopropylmethyl)-6-[1-hydroxy-1-(1-methyl-1H-benzimidazol-2-yl)methyl]-3-methylthieno[2,3-d]pyrimidin-2,4(1H,3H)-dione following the method of Example 2.

m.p. 174–175° C.; MS (+ve APCI) 381 ((M+H)$^+$); $^1$H NMR (CDCl$_3$) δ 0.42–0.48 (2H, m), 0.50–0.58 (2H, m), 1.23–1.32 (1H, m), 3.41 (3H, s), 3.75 (3H, s), 3.79–3.81 (2H, m), 4.447–4.451 (2H, m), 7.26–7.31 (2H, m), 7.31–7.34 (2H, m), 7.75–7.80 (1H, m)

EXAMPLE 35

1-({6-[(1H-Benzimidazol-1-yl)methyl]-1,2,3,4-tetrahydro-3-methyl-1-(2-methylpropyl)-2,4-dioxothieno[2,3-d]pyrinddin-5-yl}carbonyl)pyrrolidine

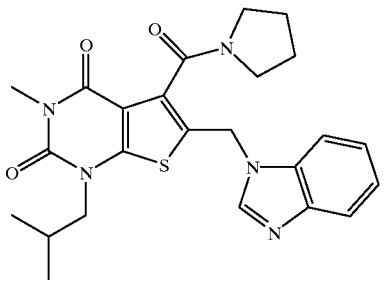

a) Diethyl 2-aminothiophene-3,4-dicarboxyate

Triethylamine (32.65 ml) was added dropwise over 15 minutes to a stirred suspension of sulfur (7.50 g), ethyl pyruvate (27.7 g) and ethyl cyanoacetate (24.9 ml) in anhydrous dimethylformamide (130 ml) at room temperature. The mixture was stirred at 50° C. for 2 hours, then cooled to room temperature and diluted with water (1l). Brine (50 ml) was added and the mixture was extracted with ether (3×250 ml). The combined organic extracts were dried over anhydrous magnesium sulfate and filtered through a large silica pad, washing with ether. The filtrate was evaporated to give the subtitle compound (33 g) as a solid.

MS (+ve APCI) 244 ((M+H)$^+$); $^1$H NMR (CDCl$_3$) δ 1.28–1.37 (6H, m), 4.11–4.33 (4H, m), 5.97 (2H, s, br), 6.60 (1H, s).

b) Diethyl 2-[(2-methylpropyl)amino]thiophene-3,4-dicarboxyate

Sodium borohydride (18 g) was added portionwise over 5 hours to a stirred suspension of diethyl 2-aminothiophene-3,4-dicarboxyate (33 g) in isobutyric acid (300 ml) at room temperature. The mixture was stirred for 16 hours then further sodium borohydride (4 g) was added and stirring was continued for 5 hours. Water (1.5l) was added, the mixture was neutralised by addition of solid sodium bicarbonate and then extracted with ether (3×500 ml). The organic extracts were dried over anhydrous magnesium sulfate, filtered and evaporated to give the subtitle compound (35 g) as a solid.

MS (+ve APCI) 300 ((M+H)$^+$); $^1$H NMR (CDCl$_3$) δ 1.00 (6H, d), 1.25–1.35 (6H, m), 1.91–2.05 (1H, m), 3.04 (2H, t), 4.20–4.33 (4H, m), 6.50 (1H, s), 7.40 (1H, s, br).

c) Ethyl 1,2,3,4-tetrahydro-3-methyl-1-(2-methylpropyl)-2,4-dioxothieno[2,3-d]pyrimidine-5-carboxylate Acetyl chloride (16.6 ml) was added dropwise to a stirred suspension of silver cyanate (36.83 g) in anhydrous toluene (250 ml) at room temperature under nitrogen. After 30 minutes, a solution of diethyl 2-[(2-methylpropyl)amino] thiophene-3,4-dicarboxyate (35 g) in anhydrous toluene (50 ml) was added. The mixture was stirred for 16 hours, then was diluted with ether (1l) and filtered. The filtrate was washed with saturated aqueous sodium bicarbonate solution (200 ml), dried over anhydrous magnesium sulfate, filtered and evaporated. The residual oil was dissolved in ethanol (300 ml), sodium ethoxide (47.7 g) was added and the mixture was stirred for 3 days. Iodomethane (43.7 ml) was added and the mixture was heated under reflux for 4 hours, then cooled to room temperature, and added to water (1.2l). The resulting suspension was acidified with 2M hydrochloric acid and then extracted with ether (3×600 ml). The organic extracts were washed with 0.2M sodium hydroxide solution (500 ml) and the aqueous layer was extracted with ether (2×500 ml). The combined organic extracts were dried over anhydrous magnesium sulfate, filtered and evaporated. The residue was purified by column chromatography over silica, eluting with ether/isohexane (1:1) to give the subtitle compound (11.34 g) as a solid.

MS (+ve APCI) 311 ((M+H)$^+$); $^1$H NMR (CDCl$_3$) δ 1.00 (6H, d), 1.40 (3H, t), 2.24–2.40 (1H, m), 3.42 (3H, s), 3.82 (2H, d), 4.42 (2H, q), 7.29 (1H, s).

d) 1,2,3,4-Tetrahydro-3-methyl-1-(2-methylpropyl)-2,4-dioxothieno[2,3-d]pyrimidine-5-carboxylic acid 2M Sodium hydroxide solution (30 ml) was added to a solution of ethyl 1,2,3,4-tetrahydro-3-methyl-1-(2-methylpropyl)-2,4-dioxothieno[2,3-d]pyrimidine-5-carboxylate (16.13 g) in methanol (25 ml) and tetrahydrofuran (50 ml). After 6 hours, further 2M sodium hydroxide solution (30 ml) was added. After a further 2 hours, water (500 ml) was added and the mixture was extracted with ether (250 ml). The aqueous layer extracts were acidified with concentrated hydrochloric acid and extracted with ethyl acetate (3×250 ml). The combined organic extracts were dried over anhydrous magnesium sulfate, filtered and evaporated. The residue was redissolved in tetrahydrofuran (100 ml) and evaporated to give the subtitle compound (13.58 g) as a solid.

MS (+ve APCI) 283 ((M+H)$^+$); $^1$H NMR (DMSO d$_6$) δ 0.95 (6H, d), 2.18–2.29 (1H, m), 3.33 (3H, s), 3.83 (2H, d), 8.08 (1H, s), 14.84 (1H, s, br).

e) 1-{[1,2,3,4-Tetrahydro-3-methyl-1-(2-methylpropyl)-2,4-dioxothieno[2,3-d]pyriniidine-5-yl]carbonyl}pyrrolidine Oxalyl chloride (1.40 ml) was added to a stirred solution of 1,2,3,4-tetrahydro-3-methyl-1-(2-methylpropyl)-2,4-dioxothieno[2,3-d]pyrimidine-5-carboxylic acid (1.51 g) and dimethylformamide (0.075 ml) in anhydrous dichloromethane (45 ml) at room temperature under nitrogen. After 2 hours, the solution was evaporated. The residue was redissolved in anhydrous dichloromethane and added to a solution of pyrrolidine (2.28 ml) in anhydrous dichloromethane (30 ml). After 30 minutes, the mixture was evaporated and the residue was purified by column chromatography over silica, eluting with ethyl acetate to give the subtitle compound (1.76 g) as a solid.

MS (+ve APCI) 336 ((M+H)$^+$); $^1$H NMR (CDCl$_3$) δ 1.00 (6H, d), 1.85–2.03 (4H, m), 2.27–2.38 (1H, m), 3.24 (2H, t),3.40 (3H, s), 3.69 (2H, t), 3.80 (2H, d), 6.88 (1H, s).

f) 1-{[1,2,3,4-Tetrahydro-6-(hydroxymethyl)-3-methyl-1-(2-methylpropyl)-2,4-dioxothieno[2,3-d]pyrimidin-5-yl]carbonyl}pyrrolidine A solution of lithium diisopropylamide (2.50 mmol) in anhydrous tetrahydrofuran (5 ml) was added dropwise to a stirred solution of 1-{[1,2,3,4-tetrahydro-3-methyl-1-(2-methylpropyl)-2,4-dioxothieno[2,3-d]pyrimidin-5-yl]carbonyl}pyrrolidine (0.42 g) in anhydrous tetrahydrofuran (10 ml) at −78° C. under nitrogen. After 10 minutes, anhydrous dimethylformamide (0.29 ml) was added. After a further 2 hours at −78° C., saturated aqueous sodium bicarbonate solution was added and the mixture was warmed to room temperature and then extracted with ethyl acetate (3×20 ml). The organic extracts were dried over anhydrous magnesium sulfate, filtered and evaporated. The residue was redissolved in methanol/acetic acid (10:1, 11 ml) and sodium borohydride (1 g) was added portionwise over 1 hour with stirring. After a further 1 hour, water (50 ml) was added, the. mixture was neutralised with sodium bicarbonate and extracted with ethyl acetate (4×25 ml). The combined organic extracts were dried over anhydrous magnesium sulfate and filtered through a silica pad which was washed with ethyl acetate/methanol (19:1). The filtrate was evaporated and the residue was purified by normal-phase preparative HPLC with gradient dichloromethane/ethanol elution to give the subtitle compound (0.22 g) as a solid.

MS (+ve APCI) 348 ((M+H—H$_2$O)$^+$); $^1$H NMR (CDCl$_3$) δ 0.99 (3H, d), 1.01 (3H, d), 1.82–2.05 (4H, m), 2.24–2.41 (1H, m), 3.04 (1H, dd), 3.12–3.20 (1H, m), 3.29–3.34 (1H, m), 3.39 (3H, s), 3.59–3.69 (1H, m), 3.71–3.79 (2H, m), 3.86 (1H, dd), 4.55 (1H, dd), 4.81 (1H, dd).

g) 1-{[6-(Chloromethyl)-1,2,3,4-tetrahydro-3-methyl-1-(2-methylpropyl)-2,4-dioxothieno[2,3-d]pyrimidin-5-yl]carbonyl}pyrrolidine Thionyl chloride (0.046 ml) was added to a solution of 1-{[1,2,3,4-tetrahydro-6-(hydroxymethyl)-3-methyl-1-(2-methylpropyl)-2,4-dioxothieno[2,3-d]pyrimidin-5-yl]carbonyl }pyrrolidine (0.1 15 g) in anhydrous dichloromethane (5 ml) under nitrogen. After 1 hour, the mixture was evaporated. The residue was redissolved in ethyl acetate (25 ml), washed with saturated aqueous sodium bicarbonate solution, dried over anhydrous magnesium sulfate, filtered and evaporated to give the subtitle compound (0.11 g) as an oil.

MS (+ve APCI) 348 ((M+H—Cl)$^+$); $^1$H NMR (CDCl$_3$) δ 1.00 (6H, d), 1.85–2.05 (4H, m), 2.27–2.36 (1H, m), 3.22–3.33 (2H, m), 3.39 (3H, s), 3.62–3.72 (2H, m), 3.75–3.82 (1H, m), 3.89 (1H, dd), 4.61 (1H, d), 4.83 (1H, d).

h) 1-({6-[(1H-Benzimidazol-1-yl)methyl]-1,2,3,4-tetrahydro-3-methyl-1-(2-methylpropyl)-2,4-dioxothieno[2,3-d]pyrinddin-5-yl}carbonyl)pyrrolidine A mixture of 1-{[6-(chloromethyl)-1,2,3,4-tetrahydro-3-methyl-1-(2-methylpropyl)-2,4-dioxothieno[2,3-d]pyrimidin-5-yl]carbonyl}pyrrolidine (0.068 g), potassium carbonate (0.10 g) and benzimidazole (0.031 g) in anhydrous dimethylformamide (3 ml) was stirred at room temperature for 16 hours. Water (30 ml) was added, then the mixture was extracted with ethyl acetate (2×30 ml). The combined organic extracts were dried over anhydrous magnesium sulfate and filtered through a silica pad which was washed with ethyl acetate. The filtrate was evaporated and the residue was purified by normal-phase preparative HPLC with gradient ethyl acetate/isohexane elution. The product was further purified by recrystallisation from ethyl acetate/isohexane to give the title compound (0.032 g).

m.p. 159–161° C.; MS (+ve APCI) 466 ((M+H)$^+$); $^1$H NMR (CDCl$_3$) δ 0.98 (6H, d), 1.35–1.44 (1H, m), 1.66–1.73 (1H, m), 1.75–1.81 (1H, m), 1.81–1.90 (1H, m), 2.26–2.33 (2H, m), 2.98–3.04 (1H, m), 3.36 (3H, s), 3.45–3.52 (1H, m), 3.62–3.72 (2H, m), 3.84 (1H, dd), 5.27 (1H, d), 5.65 (1H, d), 7.27–7.33 (2H, m), 7.44–7.47 (1H, m), 7.80–7.82 (1H, m), 8.00 (1H, s).

EXAMPLE 36

1-({1,2,3,4-Tetrahydro-6-[(1-methyl-1H-benzimidazol-2-yl)methyl]-1-(cyclopropylmethyl)-3-methyl-2,4-dioxothieno[2,3-d]pyrimnidin-5-yl}carbonyl)azetidine

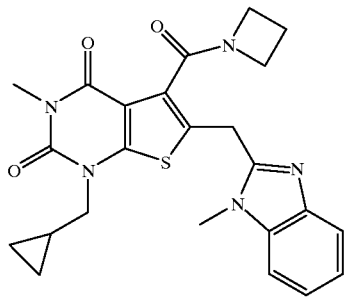

a) Diethyl 2-[(cyclopropylmethyl)amino]thiophene-3,4-dicarboxyate

Sodium borohydride (12.5 g) was added portionwise over 3 hours to a stirred solution of diethyl 2-aminothiophene-3,4-dicarboxyate (Example 36a, 25 g) in cyclopropane carboxylic acid (125 ml). The mixture was stirred at room temperature for 18 hours then further sodium borohydride (5 g) was added and stirring was continued at 50° C. for 16 hours. Further sodium borohydride (5 g) was again added and stirring was continued at 50° C. for 16 hours and then at room temperature for 3 days. Water (500 ml) was added, the mixture was neutralised with sodium bicarbonate and extracted with ether (2×250 ml). The organic extracts were dried over anhydrous magnesium sulfate, filtered and evaporated. The residue was purified by column chromatography over silica, eluting with ether/isohexane (2:3) to give the subtitle compound (12.10 g) as an oil.

MS (+ve APCI) 298 ((M+H)$^+$); $^1$H NMR (CDCl$_3$) δ 0.27–0.31 (2H, m), 0.56–0.62 (2H, m), 1.11–1.21 (1H, m), 1.30 (3H, s), 1.36 (3H, s), 3.07 (2H, dd), 4.24 (2H, q), 4.30 (2H, q), 6.51 (1H, s), 7.64 (1H, t, br).

b) Ethyl 1,2,3,4-tetrahydro-1-(cyclopropylmethyl)-3-methyl-2,4-dioxothieno[2,3-d]pyrimidine-5-carboxylate Prepared from diethyl $^2$-[(cyclopropylmethyl)amino]thiophene-3,4-dicarboxyate (12.1 g) following the procedure of Example 35 step c to give the subtitle compound (11.8 g) as an oil.

MS (+ve APCI) 309 ((M+H)$^+$); $^1$H NMR (CDCl$_3$) δ 0.49–0.53 (2H, m), 0.59–0.63 (2H, m), 1.28–1.38 (1H, m), 1.40 (3H, t), 3.43 (3H, s), 3.91 (2H, d), 4.41 (2H, q), 7.30 (1H, s).

c) 1-{[1-(Cyclopropylmethyl)-1,2,3,4-tetrahydro-3-methyl-2,4-dioxothieno[2,3-d]pyrimidin-5-yl]carbonyl}azetidine 2M Sodium hydroxide solution (6 ml) was added to a stirred solution of ethyl 1,2,3,4-tetrahydro-1-(cyclopropylmethyl)-3-methyl-2,4-dioxothieno[2,3-d]pyrimidine-5-carboxylate (3.00 g) in methanol/tetrahydrofuran (1:2, 15 ml). After 1 hour, water (200 ml) was added and the mixture was extracted with ether (50 ml). The aqueous phase was acidified with concentrated hydrochloric acid and then extracted with ethyl acetate (2×100 ml). The organic extracts were dried over anhydrous magnesium sulfate, filtered and evaporated. The resulting solid was dissolved in anhydrous dichloromethane (60 ml). Dimethylformamide (0.1 ml) was added followed by oxalyl chloride (1.70 ml). The mixture was stirred for 2 hours at room temperature and was then evaporated. The residual oil was redissolved in anhydrous tetrahydrofuran (60 ml) and added to a stirred solution of azetidine hydrochloride (2 g) in 1M sodium hydroxide solution (32 ml). After 1 hour, saturated aqueous sodium bicarbonate solution (60 ml) was added and the mixture was extracted with ethyl acetate (5×60 ml). The combined organic extracts were dried over anhydrous magnesium sulfate, filtered and evaporated. The residue was purified by column chromatography over silica, eluting with methanol/ethyl acetate (1:49) to give the subtitle compound (1.67 g) as a solid.

MS (+ve APCI) 320 ((M+H)$^+$); $^1$H NMR (CDCl$_3$) δ 0.48–0.53 (2H, m), 0.56–0.64 (2H, m), 1.25–1.36 (1H, m), 2.20–2.30 (2H, m), 3.43 (3H, s), 3.89 (2H, d), 4.14 (2H, t), 4.25 (2H, t), 6.92 (1H, s).

d) 1-({1,2,3,4-Tetrahydro-6-[hydroxy(1-methyl1H-benzinidazol-2-yl)methyl]-1-(cyclopropylmethyl)-3-methyl-2,4-dioxothieno[2,3-d]pyrimnidin-5-yl}carbonyl)azetidine A solution of lithium diisopropylamide (3.13 mmol) in anhydrous tetrahydrofuran (5 ml) was added dropwise to a stirred solution of 1-{[1-(cyclopropylmethyl)-1,2,3,4-tetrahydro-3-methyl-2,4-dioxothieno[2,3-d]pyrimidin-5-yl]carbonyl}azetidine (0.50 g) in anhydrous tetrahydrofuran (5 ml) at −78° C. under nitrogen. After 10 minutes, 2-formyl-1-methylbenzimidazole (0.501 g) was added. The mixture was stirred for 10 minutes then warmed to room temperature. The reaction was quenched with saturated aqueous sodium bicarbonate solution (30 ml) and then extracted with ethyl acetate (3×30 ml). The organic extracts were dried over anhydrous magnesium sulfate, filtered and evaporated. The residue was purified by column chromatography over silica, eluting with ethyl acetate/methanol (99:1) to give the subtitle compound (0.395 g) as a solid.

MS (+ve APCI) 480 ((M+H)$^+$).

e) 1-({1,2,3,4-Tetrahydro-6-[(1-methyl-1H-benzinidazol-2-yl)methyl]-1-(cyclopropylmethyl)-3-methyl-2,4-dioxothieno[2,3-d]pyrimidin-5-yl}carbonyl)azetidine Acetic anhydride (0.11 5 ml) was added to a solution of 1-({1,2,3,4-tetrahydro-6-[hydroxy(1-methyl-1H-benzimidazol-2-yl)methyl]-1-(cyclopropylmethyl)-3-methyl-2,4-dioxothieno[2,3-d]pyrimidin-5-yl}carbonyl)azetidine (295 mg), triethylamine (0.171 ml) and 4-dimethylaminopyridine (6 mg) in anhydrous dichloromethane (10 ml). After 1 hour, the mixture was added to saturated aqueous sodium bicarbonate solution (25 ml) and then extracted with ethyl acetate (25 ml). The organic extracts were dried over anhydrous magnesium sulfate, filtered and evaporated. The residue was redissolved in methanol (10 ml) and palladium on charcoal (10%, 70 mg) was added. The mixture was stirred under 6 atmospheres of hydrogen for 48 hours, filtered through a kieselguhr pad and evaporated. The residue was redissolved in ethyl acetate (5 ml) and filtered through a small silica pad, washing with ethyl acetate/methanol (49:1). The filtrate was evaporated and the residue was purified by normal-phase preparative HPLC with gradient dichloromethane/ethanol elution. The product was further purified by reverse-phase preparative HPLC to give the title compound (27 mg) as a solid.

MS (+ve APCI) 464 ((M+H)$^+$); $^1$H NMR (CDCl$_3$) δ 0.42–0.50 (2H, m), 0.52–0.59 (2H, m), 1.20–1.32 (1H, m), 2.10–2.37 (2H, m), 3.41 (3H, s), 3.75–3.87 (6H, m), 3.95–4.06 (2H, m), 4.25–4.38 (1H, m), 4.45 (2H, s), 7.27–7.36 (3H, m), 7.75–7.78 (1H, m).

EXAMPLE 37

5-[(3-Hydroxypropyl)thio]-3-methyl-1-(2-methylpropyl)-6-[(pyridin-3-yl)carbonyl]thieno[2,3-d]pyrimidine-2,4(1H,3H)-dione

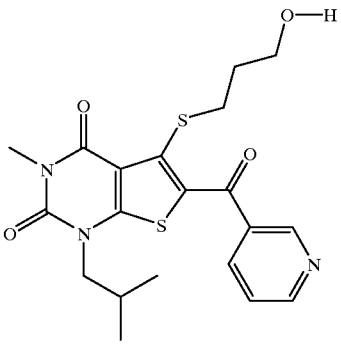

a) 6-Bromo-3-methyl-1-(2-methylpropyl)thieno[2,3-d]pyrinidine-2,4(1H,3H)-dione

To a solution of 3-methyl-1-(2-methylpropyl)thieno[2,3-d]pyrimidin-2,4(1H,3H)-dione (0.56 g, WO98/54190) in dry dichloromethane (20 ml) was added bromine (0.13 ml) in dry dichloromethane (5 ml) dropwise. The reaction was stirred for 30 minutes at room temperature. The solution was concentrated under reduced pressure. The residue was dissolved in ethyl acetate and washed with sodium metabisulfite solution. The organic layer was dried over anhydrous magnesium sulfate, filtered and concentrated under reduced pressure to give the subtitle compound as a cream solid.(0.75 g).

MS(+ve APCI) 318[M+H]$^+$; $^1$H NMR (CDCl$_3$) δ 0.99 (6H, d); 2.26–2.36(1H, m); 3.41(3H, s); 3.72(2H, d); 7.34 (1H, s).

b) 5-Bromo-3-methyl-1-(2-methylpropyl)-6-[1-hydroxy-1-(pyridin-3-yl)methyl]thieno[2,3-d]pyrimidine-2,4(1H,3H)-dione To a solution of 6-bromo-3-methyl-1-(2-methylpropyl)thieno[2,3-d]pyrimidin-2,4(1H,3H)-dione(0.75 g) in dry tetrahydrofuran (20 ml) at −78° C. was added lithium diisopropylamide (2M in tetrahydrofuran, 1.3 ml). After 15 minutes, a solution of 3-pyridinecarboxaldehyde (0.27 g) in dry tetrahydrofuran (10 ml) was added and the reaction was stirred for 3 hours at −78° C. The reaction mixture was poured into saturated ammonium chloride solution and allowed to warm to room temperature. The mixture was extracted with ethyl acetate and the combined extracts were washed with water, dried over anhydrous magnesium sulfate, filtered and concentrated under reduced pressure. The residue was purified by column chromatography over silica eluting with ethyl acetate:isohexane (1:1) to give the subtitle compound as a cream solid (0.5 g).

m.p. 132° C.; MS(+ve APCI) 424/426 [M+H]$^+$; $^1$H NMR (CDCl$_3$) δ 0.96 (6H, d); 2.09 (1H, br.s); 2.22–2.34 (1H, m); 3.40 (3H, s); 3.68–3.85 (2H, m); 6.29 (1H, s); 7.32 (1H, dd); 7.81 (1H, d); 8.52 (1H, br.d); 8.69 (1H, s).

c) 5-Bromo-3-methyl-1-(2-methylpropyl)-6-[(pyridin-3-yl)carbonyl]thieno[2,3-d]pyrimidine-2,4(1H,3H)-dione A solution of 5-bromo-3-methyl-1-(2-methylpropyl)-6-[1-hydroxy-1-(pyridin-3-yl)methyl]thieno[2,3-d]pyrimidine-2,4(1H,3H)-dione (0.50 g, Example 39 step b)), 4-methylmorpholine-N-oxide (0.21 g), powdered 4A sieves (0.58 g) and tetra-n-propylammoniumperruthenate (0.02 g) in dry dichloromethane (40 ml) was stirred for 1 hour at room temperature. The suspension was filtered through celite and the filtrate was concentrated under reduced pressure. The residue was purified by column chromatography over silica eluting with dichloromethane to give the subtitle compound as a cream solid (0.47 g).

m.p. 205° C.; MS(+ve APCI) 463 [M+CH₃CN]⁺; ¹H NMR(CDCl₃) δ 1.03 (6H, d); 2.31–2.40 (1H, m); 3.44 (3H, s); 3.87 (2H, d); 7.46 (1H, dd); 8.04–8.07 (1H, m); 8.83 (1H, br.d); 8.98 (1H, br.s).

d) 5-[(3-Hydroxypropyl)thio]-3-methyl-1-(2-methylpropyl)-6-[(pyridin-3-yl)carbonyl]thieno[2,3-d]pyrimidine-2,4(1H,3H)-dione To a suspension of sodium hydride (0.068 g) in dry tetrahydrofuran (25 ml) was added dropwise a solution of 3-mercaptopropanol (0.14 g) in dry tetrahydrofuran (5 ml). After 15 minutes, a solution of 5-bromo-3-methyl-1-(2-methylpropyl)-6-[(pyridin- 3-yl)carbonyl]thieno[2,3-d]pyrimidine-2,4(1H,3H)-dione (0.60 g, Example 39 step c) in dry tetrahydrofuran (20 ml) was added dropwise and the reaction was stirred for 3 hours at room temperature. The solution was poured into water and extracted with ethyl acetate. The combined extracts were dried over anhydrous magnesium sulfate, filtered and concentrated under reduced pressure. The residue was purified by normal-phase HPLC eluting with a gradient of 0–5% ethanol in dichloromethane to give the title compound as a cream solid (0.35 g).

m.p. 152–155° C.; MS(ES) 434[M+H]⁺; ¹H NMR (CDCl₃) δ 1.03 (6H, d); 1.72–1.64 (2H, m); 2.30–2.42 (1H, m); 2.79 (1H, t); 3.09 (2H, t); 3.44 (3H, s); 3.60 (2H, q), 3.86 (2H, d); 7.49–7.45 (1H, m); 8.10–8.07 (1H, m); 8.80 (1H, dd); 8.96 (1H, d).

EXAMPLE 38

5-[(3-Hydroxypropyl)thio]-3-methyl-1-(2-methylpropyl)-6-[1-hydroxy-1-(pyridin-3-yl)methyl]thieno[2,3-d]pyrimidine-2,4(1H,3H)-dione

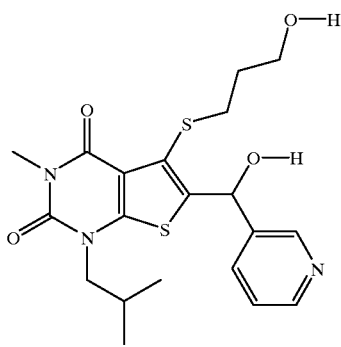

To a solution of 5-[(3-hydroxypropyl)thio]-3-methyl-1-(2-methylpropyl)-6-[(pyridin-3-yl)carbonyl]thieno[2,3-d]pyrimidine-2,4(1H,3H)-dione (0.35 g, Example 37) in dry ethanol (40 ml) at 0° C. was added sodium borohydride (0.03 g). The reaction was allowed to warm to room temperature and stirred for 2 hours. The solution was concentrated under reduced pressure. The residue was partitioned between ethyl acetate and water. The organic layer was dried over anhydrous magnesium sulfate, filtered and concentrated under reduced pressure. The residue was purified by normal-phase HPLC eluting with a gradient of 0–5% ethanol in dichloromethane to give the title compound as a white foam. (0.27 g).

MS(ES) 436[M+H]⁺; ¹H NMR(CDCl₃) δ 0.96(6H, dd); 1.84–1.76 (2H, m); 2.21–2.33 (1H, m); 2.93 (1H, quint); 2.97 (1H, br.s); 3.12 (1H, quint); 3.40 (3H, s); 3.73–3.68 (2H, m); 3.85–3.80 (2H, m); 4.25 (1H, br.s); 6.61 (1H, s); 7.31 (1H, dd); 7.80–7.77 (1H, m); 8.52–850 (1H, m); 8.70 (1H, d).

EXAMPLE 39

5-[(3-Hydroxypropyl)thio]-3-methyl-1-(2-methylpropyl)-6-[1-(pyridin-3-yl)methyl]thieno[2,3-d]pyrimidine-2,4(1H,3H)-dione

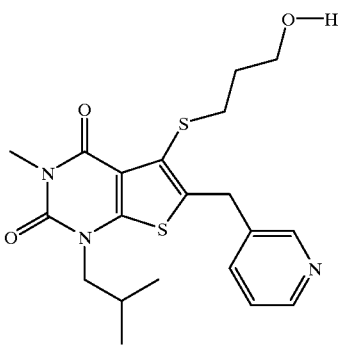

To a solution of 5-[(3-hydroxypropyl)thio]-3-methyl-1-(2-methylpropyl)-6-[1-hydroxy-1-(pyridin-3-yl)methyl]thieno[2,3-d]pyrimnidine-2,4(1H,3H)-dione (0.13 g, Example 38) in trifluoroacetic acid (4 ml) was added triethylsilane (2 ml) and the reaction was stirred for 4 hours at room temperature. The solution was concentrated under reduced pressure. The residue was basified with saturated sodium bicarbonate solution and extracted with ethyl acetate. The combined extracts were dried over anhydrous magnesium sulfate, filtered and concentrated under reduced pressure. The residue was dissolved in methanol (20 ml) and stirred at room temperature with sodium hydrogen carbonate (0.07 g) for 1 hour. The solution was concentrated under reduced pressure and the residue partitioned between ethyl acetate and water. The organic layer was dried over anhydrous magnesium sulfate, filtered and concentrated under reduced pressure. The residue was purified by normal phase HPLC eluting with a gradient of 0–5% ethanol in dichloromethane to give the title compound as a white solid (0.074 g).

m.p. 119–121° C.; MS(ES) 420[M+H]⁺; ¹H NMR (CDCl₃) δ 0.95 (6H, d); 1.83 (2H, quint); 2.19–2.31 (1H, m); 2.81 (1H, t); 3.05 (2H, t); 3.42 (3H, s); 3.74 2H, d); 3.83 (2H, q), 4.33 (2H, s); 7.26–7.23 (1H, m); 7.53–7.51 (1H, m); 8.51–8.50 (1H, m); 8.54 (1H, d).

EXAMPLE 40

3-Methyl-1-(2-methylpropyl)-6-[(pyridin-3-yl)carbonyl]-5-[(2-thienyl)thio]thieno[2,3-d]pyrimidine-2,4(1H,3H)-dione

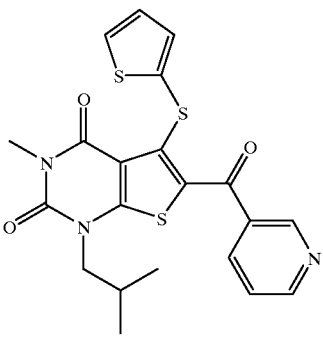

Prepared according to the method described in Example 38 from sodium hydride (0.068 g), 2-mercaptothiophene (0.15 ml), dry tetrahydrofuran (60 ml) and 5-bromo-3-methyl-1-(2-methylpropyl)-6-[(pyridin-3-yl)carbonyl]thieno[2,3-d]pyrimidine-2,4(1H,3H)-dione (0.60 g, Example 39) with stirring at room temperature for 18 hours. After work up, the residue was purified by column chromatography over silica eluting with ethyl acetate:isohexane (1:1) to give the title compound as a yellow solid (0.46 g).

m.p. 111–115° C.; MS(ES) 458[M+H]⁺; ¹H NMR (CDCl₃) δ 1.02 (6H, d); 2.29–2.41 (1H, m); 3.45 (3H, s); 3.84 (2H, d); 6.50 (1H, dd); 6.68–6.65 (1H, m); 7.19 (1H, d); 7.36–7.32 (1H, m); 7.91–7.87 (1H, m); 8.75 (1H, dd); 8.81 (1H, d).

EXAMPLE 41

3-Methyl-1-(2-methylpropyl)-6-[-(pyridin-3-yl)methyl]-5-[(2-thienyl)thio]thieno[2,3-d]pyrinidine-2,4(1H,3H)-dione

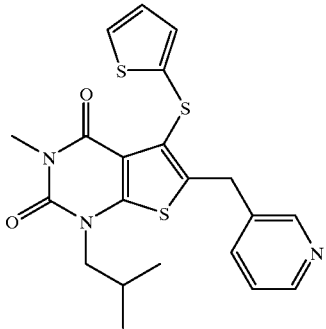

To a solution of titanium tetrachloride (1.0 ml) and 3-methyl-1-(2-methylpropyl)-6-[(pyridin-3-yl)carbonyl]-5-[(2-thienyl)thio]thieno[2,3-d]pyrimidine-2,4(1H,3H)-dione (0.46 g, Example 40) in dry dichloromethane (30 ml) at 0° C., was added dimethylamine borane complex (0.118 g) in dry dichloromethane (10 ml). The reaction was allowed to warm to room temperature and stirred for 4 hours. Hydrochloride acid (2M, 40 ml) was added cautiously and the resulting solution was extracted with dichloromethane. The combined extracts were washed with brine, dried over anhydrous magnesium sulfate, filtered and concentrated under reduced pressure. The residue was purified by column chromatography over silica eluting with a gradient of 0–10% ethanol in dichloromethane to give the title compound as a white solid (0.10 g).

m.p. 95–97° C.; MS(ES) 444[M+H]⁺; ¹H NMR(CDCl₃) δ 0.93 (6H, d); 2.15–2.27 (1H, m); 3.41 (3H, s); 3.70 (2H, d); 4.44 (2H, s); 6.95–6.92 (1H, m); 7.30–7.22 (2H, m); 7.35–7.33 (1H, m); 7.52–7.49 (1H, m); 8.54–852 (2H, m).

EXAMPLE 42

5-(3-Hydroxypropoxy)-3-methyl-1-(2-methylpropyl)-6-[1-(pyridin-3-yl)methyl]thieno[2,3-d]pyrimidine-2,4(1H,3H)-dione

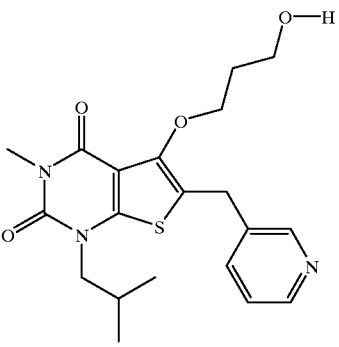

a) Methyl 2-[(1,2,3,6-tetrahydro-1,3-dimethyl-2,6-dioxo-4-pyrimidinyl)thio]acetate 6-Chloro-3-methyl-1-(2-methylpropyl)-1H-pyrimidine-2,4(1H,3H)-dione (WO 98/514190) (3.37 g) was dissolved in dimethylformamide (21 ml) and sodium hydride (60% dispersion in oil, 621 mg) was added. Methyl thioglycolate (1.45 ml) was added dropwise and the mixture was stirred at ambient temperature. After 30 minutes aqueous ammonium chloride was added and the mixture was extracted twice with ca 1:1 ether:ethyl acetate. The organic phases were combined, washed with brine, dried, filtered and evaporated. The residue was triturated with isohexane to give the subtitle compound (2.43 g). m.p. 96–97.5° C.; MS (+ve APCI) 287 ((M+H)⁺); ¹H NMR (DMSO d₆) δ 0.88 (6H, d), 2.08–2.16 (1H, m), 3.14 (3H, s), 3.69 (3H, s), 3.76 (2H, d), 4.20 (2H, s), 5.60 (1H, s).

b) 3-Methyl-1-(2-methylpropyl)-6-(3-pyridinylmethylidene)thieno[2,3-d]pyrimidine-2,4,5(1H,3H,6H)-trione Methyl 2-[(1,2,3,6-tetrahydro-1,3-dimethyl-2,6-dioxo-4-pyrimidinyl)thio]acetate (2.83 g) and pyridine-3-carboxaldehyde (2.9 ml) were dissolved in methanesulfonic acid (28 ml) and the mixture was heated to 110° C. for 18 h. The reaction was allowed to cool and was then extracted thrice with dichloromethane. The organic phases were washed with sodium bicarbonate (aqueous) and brine, dried, filtered and evaporated to give a brown residue. The aqueous phase was made alkaline by addition of sodium hydroxide and was then extracted thrice with dichloromethane, the extracts were dried, filtered and evaporated to give a second crop. Chromatography of the two batches of impure product (eluent ethyl acetate) gave the subtitle compound (2.00 g).

m.p. 215–216° C.; MS (+ve APCI) 344 ((M+H)⁺); ¹H NMR (DMSO d₆) δ 0.97 (6H, d), 2.15–2.29 (1H, m), 3.20 (3H, s), 3.82 (2H, d), 7.61 (1H, dd), 7.96 (1H, s), 8.18 (1H, dt), 8.68 (1H, dd), and 8.99 (1H, d).

c) 5-{3-[(Tetrahydro-2H-pyran2-yl)oxy]propoxy}-3-methyl-1-(2-methylpropyl)-6-[(3-pyridinyl)methyl]thieno[2,3-d]pyrimidine-2,4(1H,3H)-dione 3-Methyl-1-(2-methylpropyl)-6-(3-pyridinylmethylidene)thieno[2,3-d]pyrimidine-2,4,5(1H,3H,6H)-trione (0.85 g), triethylsilane (2 ml) and chlorotris(triphenylphosphine)rhodium(I) (34 mg) were suspended in tetrahydrofuran (10 ml) containing dimethylformamide (5 ml) and the mixture was heated to 85° C. for 18 h, then allowed to cool. The tetrahydrofuran was removed by evaporation and isohexane was added. The dark lower layer was separated and the isohexane layer was washed with 2 small portions of dimethylformamide. The dimethylformamide layers contained 3-methyl-1-(2-methylpropyl)-6-[(3-pyridinyl)methyl]-5-triethylsilyloxythieno[2,3-d]pyrimidine-2,4(1H,3H)-dione (MS (+ve APCI) 460 ((M+H)$^+$). 1-Bromo-3-(2-tetrahydropyranyl)oxypropane (750 mg) was added to the dimethylformamide solution followed by tetrabutyl ammonium fluoride (940 mg) and the mixture was stirred for 1 h. Water was added and the mixture was extracted thrice with ethyl acetate. The organic phases were combined, washed with water and then brine, dried, filtered and evaporated. The residue was purified by chromatography (isohexane:ethyl acetate 1:2) to give the subtitle compound (230 mg).

$^1$H NMR (CDCl$_3$) δ 0.95 (6H, d), 1.46–1.55 (1H, m), 1.68–1.72 (1H, m), 1.76–1.83 (1H, m), 2.12 (2H, quint), 2.20–2.31 (1H, m), 3.41 (3H, s), 3.45–3.51 (1H, m), 3.61–3.67 (1H, m), 3.70 (2H, d), 3.79–3.87 (1H, m), 3.94–4.00 (1H, m), 4.07 (2H, s), 4.19–4.26 (2H, m), 4.59 (1H, t), 7.22–7.27 (1H, m), 7.56 (1H, dt), 8.50 (1H, dd), 8.53 (1H, d).

d) 5-(3-Hydroxypropoxy)-3-methyl-1-(2-methylpropyl)-6-[1-(pyridin-3-yl)methyl]thieno[2,3-d]pyrimidine-2,4(1H, 3H)-dione 5-{3-[(tetrahydro-2H-pyran-2-yl)oxy]propoxy}-3-methyl-1-(2-methylpropyl)-6-[(3-pyridinyl)methyl]thieno[2,3-d]pyrimidine-2,4(1H,3H)-dione (230 mg) was dissolved in methanol (3 ml). Toluenesulfonic acid (190 mg) was added and the mixture was stirred for 5 h. The methanol was evaporated, sodium bicarbonate (aqueous) and ethyl acetate were added and the phases were separated. The aqueous phase was extracted twice with ethyl acetate, the ethyl acetate layers were combined, washed with brine, dried, filtered and evaporated. The residue was purified by chromatography (ethyl acetate) and HPLC (dichloromethane:ethanol 100–90:0–10) then dissolved in aqueous ethanol and precipitated by addition of water to give the title compound (41 mg).

m.p. 111–112.5° C.; MS (+ve APCI) 404 ((M+H)$^+$); $^1$H NMR (DMSO d$_6$) δ 0.88 (6H, d), 1.86 (2H, quint), 2.10–2.20 (1H, m), 3.23 (3H, s), 3.59 (2H, q), 3.63 (2H, d), 4.08 (2H, t), 4.08 (2H, s), 4.51 (1H, t), 7.35 (1H, dd), 7.66 (1H, d), 8.44 (1H, dd), 8.51 (1H, d).

EXAMPLE 43

3-Methyl-6-[(1-methyl-1H-benzimidazol-2-yl)carbonyl]-5-[(1-methylethyl)thio]-1-(2-methylpropyl)-thieno[2,3-d]pyrimidine-2,4(1H,3H)-dione

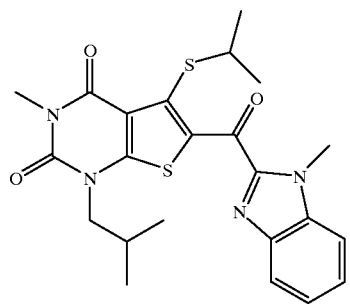

a) 5-Bromo-6-[hydroxy(1-methyl-1H-benzimidazol-2-yl)methyl]-3-methyl-1-(2-methylpropyl)-thieno[2,3-d]pyrinidine-2,4(1H,3H)dione Prepared according to the method described in Example 37 step b from 6-bromo-3-methyl-1-(2-methylpropyl)thieno[2,3-d]pyrimidin-2,4(1H,3H)-dione (5.86 g, Example 37 step a), dry tetrahydrofuran (150 ml), lithium diisopropylamide (2M, 16 ml) and 1-methyl-1H-benzimidazole-2-carboxaldehyde (3.26 g) at −78° C. for 3 hours. After work up, the residue was purified by trituration with hot ethyl acetate to give the subtitle compound as a beige solid (6.9 g).

MS (+ve APCI) 477 [M+H]$^+$; $^1$H NMR (CDCl$_3$) δ 0.82–0.93 (6H, m); 2.15–2.27 (1H, m); 3.40 (3H, s); 3.60 (1H, dd); 3.68 (3H, s); 3.82 (1H, dd); 6.46 (1H, s); 7.26–7.32 (3H, m); 7.74–7.77 (1H, m).

b) 5-Bromo-3-methyl-6-[(1-methyl-1H-benzimidazol-2-yl)carbonyl]-1-(2-methylpropyl)-thieno[2,3-d]pyrimidine-2,4(1H,3H)-dione Prepared according to the method described in Example 37 step c from 5-bromo-6-[hydroxy(1-methyl-1H-benzimidazol-2-yl)methyl]-3-methyl-1-(2-methylpropyl)-thieno[2,3-d]pyrimidine-2,4(1H,3H)-dione (5.0 g), 4-methylmorpholine-N-oxide (1.84 g), powdered 4 Å sieves (5.0 g) and tetra-n-propyl-ammonium perruthenate (0.18 g) in dry dichloromethane (170 ml) with stirring at room temperature for 24 hours. After work up, the residue was purified by column chromatography over silica eluting with a gradient of 0–2% ethanol in dichloromethane to give the subtitle compound as a yellow powder (2.93 g).

m.p. 258–258.5° C.; MS (+ve APCI) 475 [M+H]$^+$; $^1$H NMR (CDCl$_3$) δ 1.04 (6H, d); 2.35–2.47 (1H, m); 3.44 (3H, s); 3.95 (2H, d); 4.23 (3H, s); 7.40–7.46 (1H, m); 7.49–7.50 (2H, m); 7.92–7.95 (1H, m).

c) 3-Methyl-6-[(1-methyl-1H-benzimidazol-2-yl)carbonyl]-5-[(1-methylethyl)thio]-1-(2-methylpropyl)-thieno[2,3-d]pyrimidine-2,4(1H,3H)-dione Prepared according to the method described in Example 37 step d from 5-bromo-3-methyl-6-[(1-methyl-1H-benzimidazol-2-yl)carbonyl]-1-(2-methylpropyl)-thieno[2,3-d]pyrimidine-2,4(1H,3H)-dione (1.2 g), sodium hydride (0.12 g) and 2-propanethiol (0.26 ml) in dry tetrahydrofuran (150 ml) with stirring at room temperature for 19 hours. The residue was purified by flash silica chromatography eluting with a gradient of 20–50% ethyl acetate in isohexane to give the title compound as a yellow solid (0.92 g).

m.p. 166.5–169° C.; MS (+ve APCI) 471 [M+H]$^+$; $^1$H NMR (CDCl$_3$) δ 1.02 (6H, d); 1.25 (6H, d); 2.34–2.46 (1H, m); 3.45 (3H, s); 3.92 (2H, d); 3.97 (1H, q); 4.21 (3H, s); 7.38–7.46 (1H, m); 7.48–7.52 (2H, m); 7.93 (1H, d)

EXAMPLE 44

6-[Hydroxy(1-methyl-1H-benzimidazol-2-yl)methyl]-3-methyl-5-[(1-methylethyl)thio]-1-(2-methylpropyl)-thieno[2,3-d]pyrinidine-2,4(1H,3H)-dione

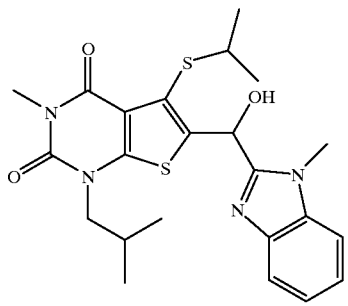

Prepared according to the method described in Example 38 from 3-Methyl-6-[(1-methyl-1H-benzimidazol-2-yl)carbonyl]-5-[(1-methylethyl)thio]-1-(2-methylpropyl)-thieno[2,3-d]pyrimidine-2,4(1H,3H)-dione (0.75 g, Example 43), sodium borohydride (0.063 g) and ethanol (150 ml) with stirring at room temperature for 2 hours. After work up, the residue was purified by flash silica chromatography eluting with ethyl acetate: isohexane (3:7) to give the title compound as a white solid (0.56 g).

m.p. 164–166° C.; MS (+ve APCI) 473 [M+H]+; 1H NMR (CDCl3) δ 0.82–0.94 (6H, m); 1.28 (6H, dd); 2.18–2.30 (1H, m); 3.42 (3H, s); 3.61 (1H, dd); 3.69 (3H, s); 3.75 (1H, quint); 3.85 (1H, dd); 4.70 (1H, d); 6.82 (1H, d); 7.31–7.33 (3H, m); 7.77–7.81 (1H, m).

EXAMPLE 45

3-Methyl-6-[(1-methyl-1H-benzimidazol-2-yl)methyl]-5-[(1-methylethyl)thio]-1-(2-methylpropyl)-thieno[2,3-d]pyrimidine-2,4(1H,3H)-dione

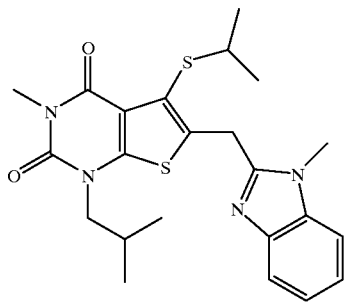

Prepared according to the method described in Example 39 from 6-[hydroxy(1-methyl-1H-benzimidazol-2-yl)methyl]-3-methyl-5-[(1-methylethyl)thio]-1-(2-methylpropyl)-thieno[2,3-d]pyrimidine-2,4(1H,3H)-dione (0.48 g, Example 44), trifluoroacetic acid (6 ml) and triethylsilane (3 ml) with stirring at room temperature for 24 hours. After work up, the residue was absorbed onto silica and purified by flash silica chromatography eluting with acetone:isohexane (1:5) to give the title compound as a white foam (0.135 g).

MS (+ve APCI) 457 [M+H]+; 1H NMR (CDCl3) δ 0.93 (6H, d); 1.29 (6H, d); 2.19–2.31 (1H, m); 3.42 (3H, s); 3.64–3.67 (1H, m); 3.70 (2H, dd); 3.76 (3H, s); 4.71 (2H, s); 7.26–7.33 (3H, m); 7.74–7.78 (1H, m)

EXAMPLE 46

3-Methyl-6-[(1-methyl-1H-benzintidazol-2-yl)methyl]-5-[(1-methylethyl)sulfonyl]-1-(2-methylpropyl)-thieno[2,3d]pyrimidine-2,4(1H,3H)-dione

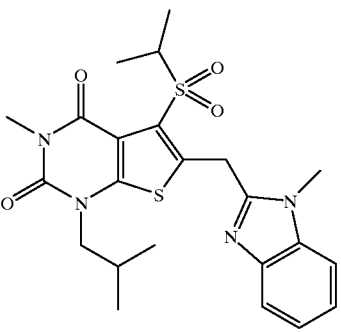

3-Chloroperoxybenzoic acid (0.13 g, 70%) was added to a solution of 3-methyl-6-[(1-methyl-1H-benzimidazol-2-yl)methyl]-5-[(1-methylethyl)thio]-1-(2-methylpropyl)-thieno[2,3-d]pyrimidine-2,4(1H,3H)-dione (0.09 g, Example 45) in dry dichloromethane (30 ml) and stirred at room temperature for 2 hours. The solution was diluted with ethyl acetate and was then washed with sodium metabisulfite solution, then with saturated sodium bicarbonate solution and then with brine. The organic layer was dried over anhydrous magnesium sulfate, filtered and evaporated. The residue was absorbed onto silica and purified by flash chromatography eluting with acetone:isohexane (1:3) to give the title compound as a foam (0.041 g).

MS (+ve APCI) 489 [M+H]+; 1H NMR (CDCl3) δ 0.95 (6H, d); 1.33 (6H, d); 2.17–2.29 (1H, m); 3.42 (3H, s); 3.76 (2H, d); 3.85 (3H, s); 4.46 (1H, quint); 5.04 (2H, s); 7.26–7.38 (3H, m); 7.73–7.76 (1H, m).

EXAMPLE 47

3-Methyl-5-[(1-methylethyl)thio]-1-(2-methylpropyl-6-(3-pyridinylcarbonyl)-thieno[2,3-d]pyrimidine 2,4(1H,3H)-dione

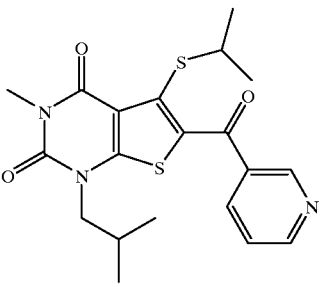

Prepared from 5-bromo-3-methyl-1-(2-methylpropyl)-6-[(pyridin-3-yl)carbonyl]thieno[2,3-d]pyrimnidine-2,4(1H,3H)-dione (Example 37 step c) and 1-methylethanethiol following the method of Example 37 step d.

m.p. 173–175° C.; MS (+ve APCI) 418 [M+H]+; 1H NMR (CDCl3) δ 1.02 (6H, d), 1.07 (6H, d), 2.30–2.42 (1H, m), 3.44 (3H, s), 3.54 (1H, quint), 3.85 (2H, d), 7.44 (1H, dd), 8.01–8.05 (1H, m), 8.79–8.82 (1H, m), 8.94–8.95 (1H, m).

EXAMPLE 48

6-(Hydroxy-3-pyridinylmethyl)-3-methyl-5-[(1-methylethyl)thio]-1-(2-methylpropyl)-thieno[2,3-d]pyrimidine-2,4(1H,3H)-dione

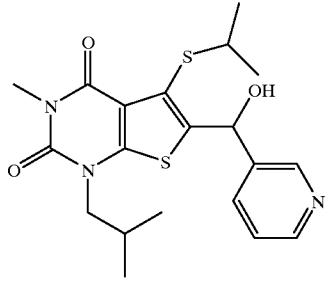

Prepared from 3-methyl-5-[(1-methylethyl)thio]-1-(2-methylpropyl)-6-(3-pyridinylcarbonyl)-thieno[2,3-d]pyrimidine 2,4(1H,3H)-dione following the method of Example 38.

m.p. 170–172° C.; MS(+ve APCI) 420 [M+H]$^+$; $^1$H NMR (CDCl$_3$) δ 0.82–0.97 (6H, m); 1.21 (3H, d); 1.27 (3H, d); 2.21–2.33 (1H, m); 3.29 (1H, d); 3.66 (3H, s); 3.68–3.83 (3H, m); 6.59 (1H, d); 7.28–7.32 (1H, m); 7.77–7.81 (1H, m); 8.52–8.54 (1H, m); 8.72 (1H, d)

EXAMPLE 49

3-Methyl-5-[(1-methylethyl)thio]-1-(2-methylpropyl)-6-(3-pyridinylmethyl)-thieno[2,3-d]pyrimidine-2,4(1H,3H)-dione

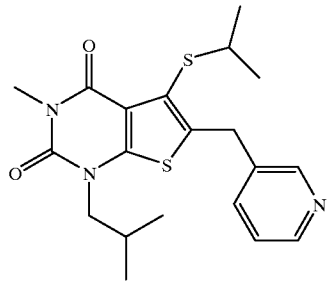

Prepared from 6-(hydroxy-3-pyridinylmethyl)-3-methyl-5-[(1-methylethyl)thio]-1-(2-methylpropyl)-thieno[2,3-d]pyrimidine-2,4(1H,3H)-dione following the method of Example 39.

MS(+ve APCI) 404 [M+H]; $^1$HNMR(CDCl$_3$) δ 0.96 (6H, d); 1.27 (6H, d); 2.20–2.32 (1H, m); 3.43 (3H, s); 3.67–3.71 (1H, m); 3.71–3.76 (2H, m); 4.40 (2H, s); 7.44–7.48 (1H, m); 7.77 (1H, d); 8.60 (1H, d); 8.63 (1H, br.s).

EXAMPLE 50

6-(1H-Benzimidazol-1-ylmethyl)-3-methyl-1-(2-methylpropyl)-5-(2-thienylthio)-thieno[2,3-d]pyrimidine-2,4(1H,3H)-dione

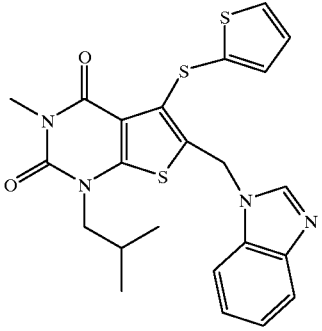

a) 5-Bromo-3-methyl-1-(2-methylpropyl)-thieno[2,3-d]pyrimidine-2,4(1H,3H)-dione

To a solution of 6-bromo-3 methyl-1-(2-methylpropyl)-thieno[2,3-d]pyrimidine-2,4(1H,3H)-dione (Example 39 step a; 5.30 g) in dry tetrahydrofuran (100 ml) at −78° C. was added lithium diisopropylamide in tetrahydrofuran (2M, 16.8 ml) dropwise over 10 minutes. After 90 minutes the reaction mixture was added to saturated ammonium chloride solution (100 ml) and left to warm to room temperature. The solution was extracted thrice with ethyl acetate, the resulting organic extracts were washed once with brine and then dried over magnesium sulfate, filtered and evaporated to leave the subtitle compound as a brown oil (4.00 g).

MS (+ve APCI) 317/319 ((M+H)$^+$).

b) 5-Chloro-1,2,3,4-tetrahydro-3-methyl-1-(2-methylpropyl)-2,4-dioxo-thieno[2,3-d]pyrimidine-6-carboxaldehyde To a solution of 5-bromo-3-methyl-1-(2-methylpropyl)-thieno[2,3-d]pyrimidine-2,4(1H,3H)-dione (4.00 g) in phosphorus trichloride (80 ml) was added dimethylformamide (1.5 ml) dropwise with stirring. The solution was heated for 18 hours at 100° C. under nitrogen. Once the solution had cooled to room temperature it was added dropwise to acidified warm water (1 ml of 2M hydrochloric acid in 500 ml of water at 50° C.) and then allowed to cool. The solution was extracted with ethyl acetate (3×200 ml). The organic phase was washed with brine and then dried over magnesium sulfate, filtered and evaporated to leave a dark brown oil. Chromatography, eluting with dichloromethane, gave a solid which was triturated with diethyl ether to give the subtitle compound as a pale yellow solid (1.76 g).

$^1$H NMR (CDCl$_3$) δ 1.00 (6H, d); 2.28–2.35 (1H, m); 3.42 (3H, s); 3.83 (2H,d); 10.10 (1H, s).

c) 1,2,3,4-Tetrahydro-3-methyl-1-(2-methylpropyl)-2,4-dioxo-5-(2-thienylthio)-thieno[2,3-d]pyrimidine-6-carboxaldehyde To a solution of 5-chloro-1,2,3,4-tetrahydro-3-methyl-1-(2-methylpropyl)-2,4-dioxo-thieno[2,3-d]pyrimidine-6-carboxaldehyde in acetone (30 ml) was added potassium carbonate (0.402 g) followed by 2-thiophene thiol (0.337 g). The reaction was stirred for 24 hours under nitrogen. The acetone was evaporated and the resulting residue was partitioned between ethyl acetate and water (1:1, 50 ml in total). The aqueous phase was extracted twice with ethyl acetate (25 ml) The organic extracts were washed with brine, then dried over magnesium sulfate, filtered and evaporated to leave a brown oil. This oil was triturated with diethyl ether to give the subtitle compound as a pale brown solid (0.528 g).

MS (+ve APCI) 381 ((M+H)⁺); ¹H NMR (DMSO d-6) δ 0.92 (6H, d); 2.15–2.22 (1H, m); 3.24 (3H, s); 3.75 (2H, d); 7.19 (1H, dd); 7.61 (1H, dd); 7.89 (1H, dd); 8.98 (1H, s).

d) 6-(Hydroxymethyl)-3-methyl-1-(2-methylpropyl)-5-(2-thienylmethyl)-thieno[2,3-d]pyrimidine-2,4(1H,3H)-dione Sodium borohydride (0.06 g) was added to 1,2,3,4-tetrahydro-3-methyl-1-(2-methylpropyl)-2,4-dioxo-5-(2-thienylthio)-thieno[2,3-d]pyrimidine-6-carboxaldehyde (0.25 g) in methanol (25 ml) and the mixture was stirred for 24 hours. The reaction was diluted with water (30 ml) and was then extracted with ethyl acetate (3×50 ml). The organic phases were washed with brine and dried over magnesium sulfate, filtered and evaporated to leave a green oil. Purification by chromatography (1:4 ethyl acetate:isohexane) gave the subtitle compound as a yellow foam (0.125 g).

MS (+ve APCI) 383((M+H)⁺); ¹H NMR (DMSO d-6) δ 0.91 (6H, d); 2.15–2.22 (1H, m); 3.24 (3H, s); 3.73 (2H, d); 4.77 (2H, d); 5.98 (1H, t); 7.00 (1H, dd); 7.31 (1H, dd); 7.57 (1H, dd).

e) 6-(Chloromethyl)-3-methyl-1-(2-methylpropyl)-5-(2-thienylthio)-thieno[2,3-d]pyrimidine-2,4(1H,3H)-dione Thionyl chloride (170 μl) was added to 6-(hydroxymethyl)-3-methyl-1-(2-methylpropyl)-5-(2-thienylmethyl)-thieno[2,3-d]pyrimidine-2,4(1H,3H)-dione (0.45 g) in dry dichloromethane (20 ml) and the mixture was stirred for 45 minutes. The solvent was evaporated to give the subtitle compound as an orange oil.

MS(+ve APCI) 411 [M+CH₃CH₂OH]⁺.

f) 6-(1H-Benzimidazol-1-ylmethyl)-3-methyl-6-(2-methylpropyl)-5-(2-thienylthio)-thieno[2,3-d]pyrimidine-2,4(1H,3H)-dione Benzimidazole (0.088 g) and sodium hydride (0.025 g of 60% dispersion) were added to 6-(chloromethyl)-3-methyl-1-(2-methylpropyl)-5-(2-thienylthio)-thieno[2,3-d]pyrimidine-2,4(1H,3H)-dione (0.20 g) in dry dimethylformamide (20 ml) and the reaction was stirred for 24 hours at room temperature. Water was added to the reaction mixture, which was then extracted with ethyl acetate (333 50 ml). The combined organic phases were washed with brine and dried over magnesium sulfate, filtered and evaporated to leave a pale brown solid. Purification by chromatography (1:3 ethyl acetate:isohexane) gave the title compound as a white solid (0.104 g).

Melting point 198° C.; MS (+ve APCI) 483 ((M+H)⁺); ¹H NMR (DMSO d-6) δ 0.86 (6H, d); 2.06–2.15 (1H, m); 3.27 (3H, s); 3.64 (2H, d); 5.93 (2H s); 6.99 (1H, m); 7.22 (2H, m); 7.38 (1H, d); 7.45 (1H, m); 7.53 (1H, d); 6.67 (1H, m); 8.28 (1H, s).

The following compounds were prepared from 6-(chloromethyl)-3-methyl-1-(2-methylpropyl)-5-(2-thienylthio)-thieno[2,3-d]pyrimidine-2,4(1H,3H)-dione and the appropriate heterocycle following the method of Example 50 step f.

| Example | Compound | m.p./ °C. | MS(+ve APCI) ((M+H)⁺) | ¹H NMR(CDCl₃)δ |
|---|---|---|---|---|
| 51 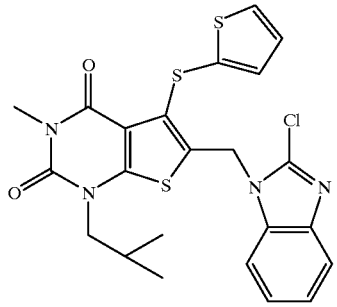 | 6-[(2-Chloro-1H-benzimidazol-1-yl)methyl-3-methyl-1-(2-methylpropyl)-5-(2-thienylthio)-thieno[2,3-d]pyrimidine-2,4(1H, 3H)-dione | 165 | | 0.81(6H, d), 2.00–2.07(1H, m), 3.22(3H, s), 3.61(2H, d), 5.97(2H, s), 7.04(1H, dd), 7.32(2H, m), 7.41(1H, d), 7.64(3H, m), |
| 52 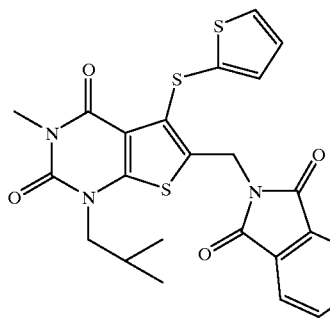 | 6-[(1,3-Dihydro-1,3-dioxo-2H-isoindol-2-yl)methyl]-3-methyl-1-(2-methylpropyl)-5-(2-thienylthio)-thieno[2,3-d]pyrimidine-2,4(1H, 3H)-dione | 163 | 512 | 0.86(6H, d), 2.09–2.16(1H, m), 3.22(3H, s), 3.68(2H, d), 5.22(2H, s), 6.99(1H, dd), 7.37(1H, d), 7.54(1H, d), 7.89(2H, dd), 7.93(2H, dd). |

EXAMPLE 53

6[Hydroxy[6-(trifluoromethyl)-2-pyridinyl]methyl]-3-methyl-1-(2-methylpropyl)-5-(2-thienylthio)-thieno[2,3-d]pyrimidine-2,4(1H,3H)-dione

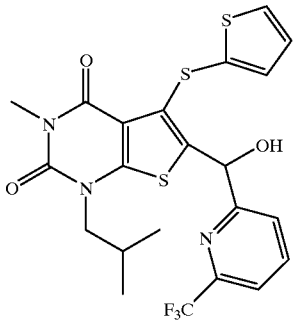

n-Butyl lithium in hexane (2.5M, 369 μl) was added dropwise to a solution of 2-bromo-6-trifluoromethylpyridine in tetrahydrofuran (8 ml) at −78° C. and the resulting solution was stirred for 1 h. 1,2,3,4-Tetrahydro-3-methyl-1-(2-methylpropyl)-2,4-dioxo-5-(2-thienylthio)-thieno[2,3-d]pyrimidine-6-carboxaldehyde (0.25 g) (Example 50, step c) in tetrahydrofuran (2 ml) was added dropwise to the lithio pyridine solution. The reaction was stirred for 3 hours at −78° C. then saturated ammonium chloride solution was added (20 ml) and the reaction was left to warm to room temperature. The reaction was extracted thrice with ethyl acetate (50 ml), then the organic phases were washed with brine and dried over magnesium sulfate, filtered and evaporated to leave a brown oil. The residue was purified by chromatography (1:4, ethyl acetate: isohexane) to give the title compound as a pale brown oil (0.03 g).

$^1$H NMR (CDCl$_3$) δ 0.90–0.99 (6H, m); 2.18–2.25 (1H, m); 3.58 (1H, dd); 3.80 (1H, dd); 4.55 (1H, d); 6.94–9.97 (1H, m); 7.10 (1H, d); 7.30–7.31 (1H, m); 7.43–7.45 (1H, m); 7.50–7.53 (1H, m); 8.06 (1H, d); 8.88 (1H, d).

EXAMPLE 54

6-(1H-Benzimidazol-1-ylmethyl)-3-methyl-5-[(1-methylethyl)thio]-1-(2-methylpropyl)-thieno[2,3-d]pyrimidine-2,4(1H,3H)-dione

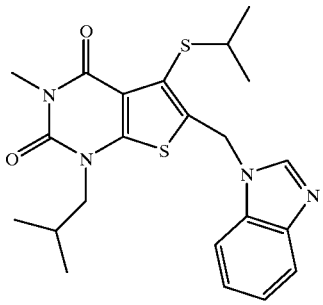

a) 1,2,3,4-Tetrahydro-3-methyl-5-[(1-methylethyl)thio]-1-(2-methylpropyl)-2,4-dioxo-thieno[2,3-d]pyrimidine-6-carboxaldehyde To a solution of 5-chloro-1,2,3,4-tetrahydro-3-methyl-1-(2-methylpropyl)-2,4-dioxo-thieno[2,3-d]pyrimidine-6-carboxaldehyde (Example 50 step b; 2 g) in dimethylformamide (20 ml) was added sodium hydride (0.3 g of 60% dispersion) followed by the addition of 2-propanethiol (0.6 g). The mixture was stirred for 24 hours at ambient temperature then the reaction was diluted with water (100 ml) and extracted thrice with ethyl acetate (3×100 ml). The organic phase was washed with water (100 ml), then with brine (100 ml) and then dried, filtered and evaporated to leave the subtitle compound as a pale yellow solid (2.24 g).

MS (+ve APCI) 341 ((M+H)$^+$; $^1$H NMR (DMSO d-6) δ 0.92 (6H, d); 1.23 (6H, d); 2.17–2.24 (1H, m); 3.26 (3H, s); 3.80 (2H, d); 3.83–3.88 (1H, m), 10.17 (1H, s).

b) 6-(Hydroxymethyl)-3-methyl-5-[(1-methylethyl)thio]-1-(2-methylpropyl)-thieno[2,3-d]pyriniidine-2,4(1H,3H)-dione Sodium borohydride (0.11 g) was added to 1,2,3,4-tetrahydro-3-methyl-5-[(1-methylethyl)thio]-1-(2-methylpropyl)-2,4-dioxo-thieno[2,3-d]pyrimidine-6-carboxaldehyde (0.50 g) in ethanol (20 ml) and the mixture was stirred for 24 hours. The reaction was diluted with water (50 ml) and was then extracted with ethyl acetate (3×50 ml). The organic phases were washed with brine and then dried, filtered and evaporated to give the subtitle compound as a yellow solid (0.45 g).

MS (+ve APCI) 325[M—H$_2$O]$^+$; $^1$H NMR (CDCl$_3$) δ 1.00 (6H, d); 1.25 (6H, d); 2.11 (1H, t); 2.30–2.37 (1H, m); 3.41 (3H, s); 3.65–3.68 (1H, m); 3.81 (2H, d); 4.95 (2H, d).

c) 6-(Chloromethyl)-3-methyl-5-[(1-methylethyl)thio]-1-(2-methylpropyl)-thieno[2,3-d]pyrimidine-2,4(1H,3H)-dione Thionyl chloride (145 μl) was added to 6-(hydroxymethyl)-3-methyl-5-[(1-methylethyl)thio]-1-(2-methylpropyl)-thieno[2,3-d]pyrimidine-2,4(1H,3H)-dione (0.45 g) in dry dichloromethane (20 ml) and the mixture was stirred for 24 hours. The solvent was evaporated to give the subtitle compound as a an oil.

d) 6-(1H-Benzimidazol-1-ylmethyl)-3-methyl-5-[(1-methylethyl)thio]-1-(2-methylpropyl)-thieno[2,3-d]pyrimidine-2,4(1H,3H)-dione Benzimidazole (0.083 g) and sodium hydride (60% dispersion, 0.031 g) were added to 6-(chloromethyl)-3-methyl-5-[(1-methylethyl)thio]-1-(2-methylpropyl)-thieno[2,3-d]pyrimidine-2,4(1H,3H)-dione (0.21 g) in dry dimethylformamide (10 ml) and the reaction was stirred for 2 hours at room temperature. Water was added to the reaction mixture which was then extracted with ethyl acetate (3×50 ml). The combined organic phases were washed with brine and dried, filtered and evaporated. The residue was triturated with diethyl ether to give the title compound (0.163 g).

m.p. 195° C.; $^1$H NMR (CDCl$_3$) δ 0.92 (6H, d); 1.31 (6H,d); 2.17–2.23 (1H, m); 3.42 (3H, s); 3.69 (2H, d); 3.76–3.83 (1H m); 5.71 (2H, s); 7.27–7.34 (2H, m); 7.45–7.47 (1H, m); 7.82–7.84 (1H, m); 8.01 (1H, s).

The following compounds were prepared from 6-(chloromethyl)-3-methyl-5-[(1-methylethyl)thio]-1-(2-methylpropyl)-thieno[2,3-d]pyrimidine-2,4(1H,3H)-dione and the appropriate heterocycle following the method of Example 54 step d.

| Example | Compound | | m.p./ °C. | MS(+ve APCI) ((M+H)+) | 1H NMR δ |
|---|---|---|---|---|---|
| 55 | 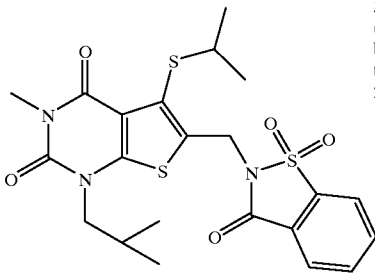 | 3-Methyl-5-[(1-methylethyl)thio]-1-(2-methylpropyl)-6-[[3-oxo-1,2-benzisothiazol-2(3H)-yl]methyl]-thieno[2,3-d]pyrimidine-2,4(1H, 3H)-dione, S,S-dioxide | 184 | 508 | (CDCl$_3$) 0.96(6H, d), 1.33 (6H, d) 2.25–2.32(1H, m), 3.43(3H, s), 3.71–3.77(1H, m), 3.76(2H, d), 5.38(2H, s), 7.85–7.95(3H, m), 8.12(1H, d). |
| 56 | 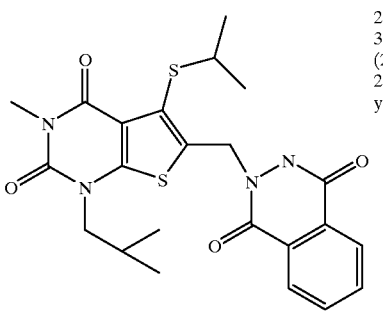 | 2,3-Dihydro-2-[[1,2,3,4-tetrahydro-3-methyl-5-[(1-methylethyl)thio]-1-(2-methylpropyl)-2,4-dioxothieno[-2,3-d]pyrimidin-6-yl]methyl]-1,4-phthalazinedione | 222 | | (DMSO d-6) 0.94(6H, d), 1.18(6H, d) 2.19–2.26(1H, m), 3.26(3H, s), 3.56–3.63 (1H, m), 3.77(2H, d), 5.64(2H, s), 7.87–7.96(3H, m), 8.24(1H, d), 12.07(1H, s). |

Pharmacological Data

Inhibition of PMA/ionomycin-stimulated Peripheral Blood Mononuclear Cell Proliferation The assay for PMA/ionomycin-stimulated PBMC proliferation was performed in 96-well flat bottomed microtitre plates. Compounds were prepared as 10 mM stock solutions in dimethyl sulfoxide. A 50-fold dilution of this was prepared in RPMI and serial dilutions were prepared from this solution. 10 μl of the 50-fold diluted stock, or dilutions of it, were added to the well to give concentrations in the assay starting at 9.5 μM and going down. Into each well was placed 1×10$^5$ PBMC, prepared from human peripheral blood from a single donor, in RPMI1640 medium supplemented with 10% human serum, 2 mM glutamine and penicillin/streptomycin. Phorbol myristate acetate (PMA) (0.5 ng/ml final concentration) and ionomycin (500 ng/ml final concentration) were added to these cells in supplemented RPMI1640 medium (as above) so that the final volume of the assay was 0.2 ml. The cells were incubated at 37° C. in a humidified atmosphere at 5% carbon dioxide for 72 hours. $^3$H-Thymidine (0.5 μCi) was added for the final 6 hours of the incubation. The level of radioactivity incorporated by the cells was then determined and this is a measure of proliferation.

The title compounds of Examples 1 to 56 were found to exhibit an IA$_{50}$ value of less than 1×10$^{-6}$ M in the above test.

What is claimed is:
1. A compound of formula (I):

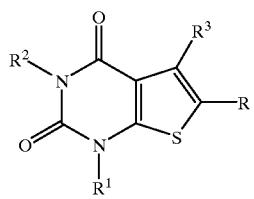

wherein:
R represents a group —C(O)Ar$^1$ or —C(R$^4$)(R$^5$)Ar$^1$;
Ar$^1$ represents a heterocyclic group comprising a total of from 5 to 10 atoms which include from 1 to 3 heteroatoms independently selected from nitrogen, oxygen and sulfur, which group Ar$^1$ may be optionally substituted by one or more substituents independently selected from oxo, hydroxyl, C$_{1-4}$alkyl, C$_{1-4}$alkoxy, halogen, trifluoromethyl, amino, nitro, cyano, trifluoromethoxy, phenoxy, —CH$_2$N(R$^6$)$_2$, —NHSO$_2$CF$_3$, C$_{1-4}$alkylsulfonylamino, —NHC(O)R$^{6a}$, CO$_2$R$^7$ or —C(O)NR$^8$R$^{8a}$, with the proviso that Ar$^1$ does not represent an optionally substituted benzofuranyl, benzothienyl, indolyl, quinolyl or isoquinolyl group;
R$^4$ represents a hydrogen atom or a C$_{1-4}$ alkyl group;
R$^5$ represents a hydrogen atom or a hydroxyl group; each R$^6$ independently represents a hydrogen atom or a C$_{1-4}$ alkyl group;
R$^{6a}$ represents a hydrogen atom or C$_{1-6}$ alkyl, phenyl, pyridinyl, (phenyl) C$_{1-4}$ alkyl or (pyridinyl) C$_{1-4}$ akyl, each of which may be optionally substituted by one or more substituents independently selected from C$_{1-4}$ alkyl, C$_{1-4}$ alkoxy, C$_{1-4}$ alkylcarbonylamino, halogen or trifluoromethyl;

59

R$^7$ represents a hydrogen atom or a C$_{1-4}$ alkyl group;
R$^8$ and R$^{8a}$ each independently represent a hydrogen atom or a C$_{1-4}$ alkyl, phenyl or pyridinyl group;
R$^1$ and R$^2$ each independently represent a hydrogen atom or a C$_{1-6}$ alkyl, C$_{3-6}$ alkenyl, CH$_2$C$_{3-5}$ cycloalkyl or C$_{3-6}$ cycloalkyl group;
R$^3$ a hydrogen atom or a group X—R$^9$ or X—Ar$^2$;
X represents an oxygen atom, S(O)$_n$, C(O)NR$^{10}$, C(O)O, NH(CO)NR$^{10}$, NH(CO)O or SO$_2$NR$^{10}$, with the proviso that when X represents an oxygen atom and R represents a group —C(R$^4$)(R$^5$)Ar$^1$, then R$^4$ and R$^5$ both represent a hydrogen atom; n is 0, 1 or 2;
R$^9$ represents a methyl group optionally substituted by one or more substituents independently selected from cyano, carboxyl, C$_{1-5}$ alkoxycarbonyl, 5-tetrazolyl or C(O)NR$^{11}$R$^{12}$, or R$^9$ represents a C$_{2-6}$ alkyl or C$_{3-6}$ alkenyl group, each of which may be optionally substituted by one or more substituents independently selected from hydroxyl, cyano, carboxyl, C$_{1-5}$ alkoxy, C$_{1-5}$ alkoxycarbonyl, 5-tetrazolyl, azido, phthalimido, SO$_2$NH$_2$, C(O)NR$^{11}$R$^{12}$, NR$^{13}$R$^{14}$, NHC(O)R$^{15}$ or NHSO$_2$R$^{16}$ where R$^{11}$, R$^{12}$, R$^{13}$ and R$^{14}$ each independently represent a hydrogen atom or a C$_{1-4}$ alkyl group, R$^{15}$ represents a C$_{1-4}$ alkyl, C$_{1-4}$ alkoxy, amino or (di)C$_{1-4}$alkylamino group or an alkoxyalkylene group containing up to 6 carbon atoms, and R$^{16}$ represents a C$_{1-4}$ alkyl or trifluoromethyl group; or, additionally, in the case where X represents C(O)NR$^{10}$, NH(CO)NR$^{10}$ or SO—NR$^{10}$, R$^9$ and R$^{10}$ together with the nitrogen atom to which they are attached may form a 4- to 7-membered saturated heterocyclic ring which may be optionally substituted by one or more hydroxyl groups;
R$^{10}$ represents a hydrogen atom or a C$_{1-6}$alkyl group or is linked to as defined above; and
Ar$^2$ is phenyl, pyridinyl, thienyl, pyridone or pyridine N-oxide, each of which may be optionally substituted by one or more substituents independently selected from halogen, hydroxyl, nitro, amino, NHSO$_2$CF$_3$, C$_{1-4}$ alkyl, C$_{1-4}$ alkoxy, bis-C$_{1-4}$alkanesulfonylamino, C$_{1-4}$alkylcarbonylamino or C$_{1-4}$alkoxycarbonylamino;
or a pharmaceutically-acceptable salt or solvate thereof.

2. A compound according to claim 1, wherein R represents a group —C(R$^4$)(R$^5$)Ar$^1$.

3. A compound according to claim 2, wherein R$^4$ represents a hydrogen atom.

4. A compound according to claim 1, wherein Ar$^1$ represents a benzimidazolyl, pyridinyl, thienyl, thiazolyl, pyrazolyl, benzotriazolyl, indazolyl, pyridopyrrolyl or benzothiazolyl group optionally substituted as defined in claim 1.

5. A compound according to claim 1, wherein R$^1$ and R$^2$ each independently represent a C$_{1-6}$ alkyl group.

6. A compound according to claim 1, wherein R$^3$ represents a hydrogen atom.

7. A compound according to claim 1 relected from:
(±)-6-[1-Hydroxy-1-(1-methyl-1H-benzimidazol-2-yl)methyl]-3-methyl-1-(2-methylpropyl)thieno[2,3-d]pyrimidine-2,4(1H,3H)-dione,
3-Methyl-6-[(1-methyl-1H-benzimidazol-2-yl)methyl]-1-(2-methylpropyl)thieno[2,3-d]pyrimidine-2,4(1H,3H)-dione,
(±)-6-[1-Hydroxy-1-(2-pyridinyl)methyl]-3-methyl-1-(2-methylpropyl)thieno[2,3-d]pyrimidine-2,4(1H,3H)-dione,
(±)-6-[1-Hydroxy-1-(3-pyridinyl)methyl]-3-methyl-1-(2-methylpropyl)thieno[2,3-d]pyrimidine-2,4(1H,3H)-dione,

60

(±)-6-[1-Hydroxy-1-(4-pyridinyl)methyl]-3-methyl-1-(2-methylpropyl)thieno[2,3-d]pyrimidine-2,4(1H,3H)-dione,
(±)-6-[1-Hydroxy-1-(2-thienyl)methyl]-3-methyl-1-(2-methylpropyl)thieno[2,3-d]pyrimidine-2,4(1H,3H)-dione,
(±)-6-[1-(5-Chloro-2-thienyl)-1-hydroxymethyl]-3-methyl-1-(2-methylpropyl)thieno[2,3-d]pyrimidine-2,4(1H,3H)-dione,
(±)-6-[1-Hydroxy-1-(3-thienyl)methyl]-3-methyl-1-(2-methylpropyl)thieno[2,3-d]pyrimidine-2,4(1H,3H)-dione,
(±)-6-[1-Hydroxy-1-(2-thiazolyl)methyl]-3-methyl-1-(2-methylpropyl)thieno[2,3-d]pyrimidine-2,4(1H,3H)-dione,
(±)-6-[1-(4-Chloro-1-methyl-1H-pyrazol-3-yl)-1-hydroxymethyl]-3-methyl-1-(2-methylpropyl)thieno[2,3-d]pyrimidine-2,4(1H,3H)-dione,
3-Methyl-1-(2-methylpropyl)-6-(2-pyridinylmethyl)thieno[2,3-d]pyrimidine-2,4(1H,3H)-dione,
3-Methyl-1-(2-methylpropyl)-6-(3-pyridinylmethyl)thieno[2,3-d]pyrimidine-2,4(1H,3H)-dione,
3-Methyl-1-(2-methylpropyl)-6-(4-pyridinylmethyl)thieno[2,3-d]pyrimidine-2,4(1H,3H)-dione,
3-Methyl-1-(2-methylpropyl)-6-(2-thienylmethyl)thieno[2,3-d]pyrimidine-2,4(1H,3H)dione,
6-(5-Chloro-2-thienylmethyl)-3-methyl-1-(2-methylpropyl)thieno[2,3-d]pyrimidine-2,4(1H,3H)-dione,
3-Methyl-1-(2-methylpropyl)-6-(2-thiazolylmethyl)thieno[2,3-d]pyrimidine-2,4(1H,3H)-dione,
6-[(4-Chloro-1-methyl-1H-pyrazol-3-yl)methyl]-3-methyl-1-(2-methylpropyl)thieno[2,3-d]pyrimidine-2,4(1H,3H)-dione,
6-[(1H-Benzimidazol-1-yl)methyl]-3-methyl-1-(2-methylpropyl)thieno[2,3-d]pyrimidine-2,4(1H,3H)-dione,
6-(2H-Benzotriazol-2-ylmethyl)-3-methyl-1-(2-methylpropyl)thieno[2,3-d]pyrimidine-2,4(1H,3H)-dione,
6-(1H-Benzotriazol-1-ylmethyl)-3-methyl-1-(2-methylpropyl) thieno[2,3-d]-pyrimidine-2,4(1H,3H)-dione,
6-(2H-Indazol-2-ylmethyl)-3-methyl-1-(2-methylpropyl)thieno[2,3-d]pyrimidine-2,4(1H,3H)-dione,
6-(1H-Indazol-1-ylmethyl)-3-methyl-1-(2-methylpropyl)thieno[2,3-d]pyrimidine-2,4(1H,3H)-dione,
3-Methyl-1-(2-methylpropyl)-6-[(1H-pyrrolo[2,3-b]pyridin-3-yl)methyl]thieno[2,3-d]pyrimidine-2,4-1H,3H)-dione,
(±)-6-[1-Hydroxy-1-(benzothiazol-2-yl)methyl]-3-methyl-1-(2-methylpropyl)thieno[2,3-d]pyrimidine-2,4(1H,3H)-dione,
6-(Benzothiazol-2-yl)methyl-3-methyl-1-(2-methylpropyl)thieno[2,3-d]pyrimidine-2,4(1H,3H)-dione,
6-[1-Hydroxy-1-(1-methyl-1H-benzimidazol-2-yl)methyl]-3-methyl-1-(1-methylethyl)thieno[2,3-d]pyrimidine-2,4(1H, 3H)-dione,
3-Methyl-6-[(1-methyl-1H-benzimidazol-2-yl)methyl]-1-(1-methylethyl)thieno[2,3-d]pyrimidine-2,4(1H, 3H)-dione,
(3R)-1-{[1,2,3,4-Tetrahydro-3-methyl-1-(2-methylpropyl)-6-(3-pyridinyl)methyl-2,4-dioxothieno[2,3-d]pyrimidin-5-yl]sulfonyl}pyrrolidin-3-ol, 1-{[1,2,3,4-Tetrahydro-3-methyl-1-(2-methylpropyl)-6-(3-pyridinyl)methyl-2,4-dioxothieno[2,3-d]pyrimidin-5-yl]sulfonyl}pyrrolidine, ±-6-[(1H-Benzimidazol-2-yl)-1-hydroxymethyl]-3-methyl-1-(2-methylpropyl)thieno[2,3-d]pyrimidine-2,4(1H,3H)-dione, 6-[(1H-Benzimidazol-1-yl)methyl]-3-methyl-1-(1-methylethyl)thieno[2,3-d]pyrimidine-2,4(1H,3H)-dione, 6-([1H-Benzimidazol-1-yl]methyl)-1-(cyclopropylmethyl)-3-methyl-thieno[2,3-9]pyrimidine-2,4(1H, 3H)-dione, 1-(Cyclopropylmethyl)-6-[1-hydroxy-1-(1-methyl-1H-benzimidazol-2-yl)methyl]-3-methylthieno[2,3-d]pyrimidin-2,4(1H,3H)-dione, 1-(Cyclopropylmethyl)-6-[(1-methyl-1H-benzimidazol-2-yl)methyl]-3-miethylthieno[2,3-d]pyrimidin-2,4(1H,3H)-dione, 1-({6-[(1H-Benzimidazol-1-yl)methyl]-1,2,3,4-tetrahydro-3-methyl-1-(2-methylpropyl)-2,4-dioxothieno[2,3-d]pyrimidin-5-yl}carbonyl)pyrrolidine, 1-({1,2,3,4-Tetrahydro-6-[(1-methyl-1H-benzimidazol-2-yl)methyl]-1-(cyclopropylmethyl)-3-methyl-2,4-dioxothieno[2,3-d]pyrimidin-5-yl}carbonyl)azetidine, 5-[(3-Hydroxypropyl)thio]-3-methyl-1-(2-methylpropyl)-6-[(pyridin-3-yl)carbonyl]thieno[2,3-d]pyrimidine-2,4(1H,3H)-dione, 5-[(3-Hydroxypropyl)thio]-3-methyl-1-(2-methylpropyl)-6-[1-hydroxy-1-(pyridin-3-yl)methyl]thieno[2,3-d]pyrimidine-2,4(1H,3H)-dione, 5-[(3-Hydroxypropyl)thio]-3-methyl-1-(2-methylpropyl)-6-[1-(pyridin-3-yl)methyl]thieno[2,3-d]pyrimidine-2,4(1H,3H)-dione, 3-Methyl-1-(2-methylpropyl)-6-[(pyridin-3-yl)carbonyl]-5-[(2-thienyl)thio]thieno[2,3-d]pyrimidine-2,4(1H,3H)-dione, 3-Methyl-1-(2-methylpropyl)-6-[1-(pyridin-3-yl)methyl]-5-[(2-thienyl)thio]thieno[2,3-d]pyrimidine-2,4(1H,3H)-dione, 5-(3-Hydroxypropoxy)-3-methyl-1-(2-methylpropyl)-6-[1-(pyridin-3-yl)methyl]thieno[2,3-d]pyrimidine-2,4(1H,3H)-dione, 3-Methyl-6-[(1-methyl-1H-benzimidazol-2-yl)carbonyl]-5-[(1-methylethyl)thio]-1-(2-methylpropyl)-thieno[2,3-d]pyrimidine-2,4(1H,3H)-dione, 6-[Hydroxy(1-methyl-1H-benzimidazol-2-yl)methyl]-3-methyl-5-[(1-methylethyl)thio]-1-(2-methylpropyl)-thieno[2,3-d]pyrimidine-2,4(1H,3H)-dione, 3-Methyl-6-[(1-methyl-1H-benzimidazol-2-yl)methyl]-5-[(1-methylethyl)thio]-1-(2-methylpropyl)-thieno[2,3-d]pyrimidine-2,4(1H,3H)-dione, 3-Methyl-6-[(1-methyl-1H-benzimidazol-2-yl)methyl]-5-[(1-methylethyl)sulfonyl]-1-(2-methylpropyl)-thieno[2,3-d]pyrimidine-2,4(1H,3H)-dione, 3-Methyl-5-[(1-methylethyl)thio]-1-(2-methylpropyl-6-(3-pyridinylcarbonyl)-thieno[2,3-d]pyrimidine 2,4(1H, 3H)-dione, 6-(Hydroxy-3-pyridinylmethyl)-3-methyl-5-[(1-methylethyl)thio]-1-(2-methylpropyl)-thieno[2,3-d]pyrimidine-2,4(1H,3H)-dione, 3-Methyl-5-[(1-methylethyl)thio]-1-(2-methylpropyl)-6-(3-pyridinylmethyl)thieno[2,3-d]pyrimidine-2,4(1H,3H)-dione, 6-(1H-Benzimidazol-1-ylmethyl)-3-methyl-1-(2-methylpropyl)-5-(2-thienylthio)-thieno[2,3-d]pyrimidine-2,4(1H,3H)-dione, 6-[(2-Chloro-1H-benzimidazol-1-yl)methyl-3-methyl-1-(2-methylpropyl)-5-(2-thienylthio)-thieno[2,3-d]pyrimidine-2,4(1H,3H)-dione, 6-[(1,3-Dihydro-1,3-dioxo-2H-isoindol-2-yl)methyl]-3-methyl-1-(2-methylpropyl)-5-(2-thienylthio)-thieno[2,3-d]pyrimidine-2,4(1H,3H)-dione, 6-[Hydroxy[6-(trifluoromethyl)-2-pyridinyl]methyl]-3-methyl-1-(2-methylpropyl)-5-(2-thienylthio)-thieno[2,3-d]pyrimidine-2,4(1H,3H)-dione, 6-(1H-Benzimidazol-1-ylmethyl)-3-methyl-5-[(1-methylethyl)thio]-1-(2-methylpropyl)-thieno[2,3-d]pyrimidine-2,4(1H,3H)-dione, 3-Methyl-5-[(1-methylethyl)thio]-1-(2-methylpropyl)-6-[[3-oxo-1,2-benzisothiazol-2(3H)-yl]methyl]-thieno[2,3-d]pyrimidine-2,4(1H,3H)-dione, S,S-dioxide, 2,3-Dihydro-2-[[1,2,3,4-tetrahydro-3-methyl-5-[(1-methylethyl)thio]-1-(2-methylpropyl)-2,4-dioxothieno[2,3-d]pyrimidin-6-yl]methyl]-1,4-phthalazinedione and their pharmaceutically acceptable salts and solvates.

8. A pharmaceutical composition comprising a compound of formula (I), or a pharmaceutically-acceptable salt or solvate thereof, according to claim 1 in association with a pharmaceutically-acceptable adjuvant, diluent or carrier.

9. A process for the preparation of a compound of formula (I) as defined in claim 1 which comprises:

(a) when $R^3$ represents a hydrogen atom or a group $X$—$R^9$ or $X$—$Ar^2$ where X represents $C(O)NR^{10}$, $C(O)O$, $NH(CO)NR^{10}$ or $NH(CO)O$ and R represents —$C(R^4)(R^5)Ar^1$ where $R^4$ is a hydrogen atom or a $C_{1-4}$ alkyl group, $R^5$ is a hydroxyl group and $Ar^1$ is attached through a carbon atom to —$C(R^4)(R^5)$, reacting a compound of general formula

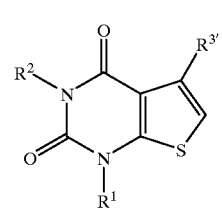

(II)

wherein $R^{3'}$ represents a hydrogen atom or a group $X$—$R^9$ or $X$—$Ar^2$ in which X represents $C(O)NR^{10}$, $C(O)O$, $NH(CO)NR^{10}$ or $NH(CO)O$, and $R^1$, $R^2$, $R^9$, $R^{10}$ and $Ar^2$ are as defined in formula (I), with a compound of general formula (III), $Ar^1$—$C(O)R^4$, wherein $R^4$ and $Ar^1$ are as defined in formula (I) and $Ar^1$ is attached through a carbon atom to —$C(O)R^4$; or (b) when R represents —$C(R^4)(R^5)Ar^1$ where $R^4$ is a hydrogen atom, $R^5$ is a hydroxyl group and $Ar^1$ is attached through a carbon atom to —$C(R^4)(R^5)$, reacting a compound of general formula

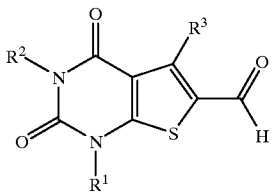

(IV)

wherein $R^1$, $R^2$ and $R^3$ are as defined in formula (I), with a compound of general formula (V), $Ar^1$—M, wherein M represents a metal ion (e.g. lithium) and $Ar^1$ is as defined in formula (I); or (c) when X represents S(O)n and R represents —C($R^4$)($R^5$)$Ar^1$ where $R^4$ is a $C_{1-4}$ alkyl group, $R^5$ is a hydroxyl group and $Ar^1$ is attached through a carbon atom to —C($R^4$)($R^5$), reacting a compound of general formula

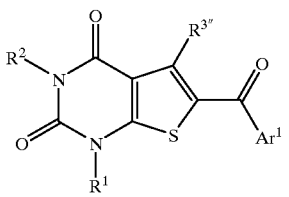

(VI)

wherein $R^{3''}$ represents S—$R^9$ or S—$Ar^2$ and $R^1$, $R^2$, $R^9$, $Ar^1$ and $Ar^2$ are as defined in formula (I), with a compound of general formula (VII), $R^{4'}$-MgHal, wherein $R^{4'}$ represents a $C_{1-4}$ alkyl group and Hal represents a halogen atom, optionally followed by an oxidation reaction; or (d) when X represents $SO_2NR^{10}$, reacting a corresponding compound of formula (I) in which $R^3$ represents a hydrogen atom, with sulphur dioxide in the presence of a base, followed by an oxidation step and then reaction with a compound of general formula (VIII), $HNR^{10}R^{17}$, where $R^{17}$ represents a group $R^9$ or $Ar^2$ and $R^9$, $R^{10}$ and $Ar^2$ are as defined in formula (I); or (e) when R represents —C($R^4$)($R^5$)$Ar^1$ where $R^5$ represents a hydrogen atom, reacting a corresponding compound of formula (I) in which $R^5$ represents a hydroxyl group, with a reducing agent; or (f) when R represents —C($R^4$)($R^5$)$Ar^1$ where $R^4$ is a hydrogen atom or a $C_{1-4}$ alkyl group, $R^5$ is a hydrogen atom and $Ar^1$ is attached through a nitrogen heteroatom to —C($R^4$)($R^5$), reacting a compound of general formula

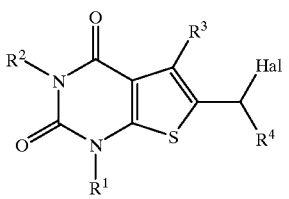

(IX)

wherein Hal represents a halogen atom and $R^1$, $R^2$, $R^3$ and $R^4$ are as defined in formula (I), with a compound of general formula (X), $Ar^1$—H, wherein $Ar^1$ is as defined in formula (I), in the presence of a base; or (g) when R reperesents a group —C(O)$Ar^1$, oxidising a corresponding compound of formula (I) in which $R^4$ is a hydrogen atom and $R^5$ is a hydroxyl group; or (h) when $R^3$ reperesent a hydrogen atom or a group X—R or X—$Ar^2$ where X represents C(O)$HR^{10}$, C(O)O, NH(CO)$NR^{10}$ or NH(CO)O and R represents a group —C(O)$Ar^1$, reacting a compound of formula (II) as defined above, with a compound of general formula (XI), $Ar^1CON(CH_3)OCH_3$ wherein $Ar^1$ is as defined in formula (I), in the presence of a base; or (j) when X represents an oxygen atom and R represents a group —C(O)$Ar^1$, reacting a compound of general formula

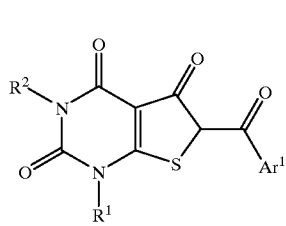

(XII)

wherein $R^1$, $R^2$ and $Ar^1$ are as defined in formula (I), with a compound of general formula (XIII), $R^{17}$—L, wherein L represents a leaving group and $R^{17}$ is as defined in (d) above; or (k) when X represents an oxygen atom and R represents a group —$CH_2Ar^1$, reacting a compound of general formula

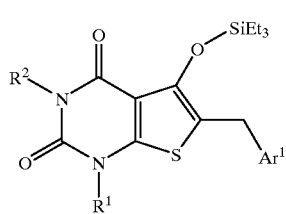

(XIV)

with a compound of formula (XIII) as defined in (j) above;

and optionally after (a), (b), (c), (d), (e), (f), (g), (h), (j) or (k) converting the compound of formula (I) to a further compound of formula (I) and, if desired, forming a pharmaceutically acceptable salt or solvate thereof.

10. A process for the preparation of a pharmaceutical composition as claimed in claim 8 which comprises mixing a compound of formula (I), or a pharmaceutically-acceptable salt or solvate thereof, according to claim 1 with a pharmaceutically-acceptable adjuvant, diluent or carrier.

11. A method of treating allograft rejection which comprises administering to a patient a therapeutically effective amount of a compound (I) or a pharmaceutically acceptable salt or solvate thereof, as claimed in claim 1.

12. A method of treating, or reducing the risk of, a reversible obstructive airways disease in a patient suffering from, or at risk of, said disease, which comprises administering to the patient a therapeutically effective amount of a compound of formula (I), or a pharmaceutically-acceptable salt or solvate thereof, as claimed in claim 1.

* * * * *